United States Patent
Spruce

(10) Patent No.: US 8,961,428 B2
(45) Date of Patent: Feb. 24, 2015

(54) FORCE TRANSDUCER, MEDICAL INSTRUMENT, AND MACHINE IMPLEMENTED METHOD

(76) Inventor: Ian James Spruce, Forum (GB)

(*) Notice: Subject to any disclaimer, the term of this patent is extended or adjusted under 35 U.S.C. 154(b) by 975 days.

(21) Appl. No.: 12/612,983

(22) Filed: Nov. 5, 2009

(65) Prior Publication Data

US 2010/0113966 A1    May 6, 2010

Related U.S. Application Data

(60) Provisional application No. 61/111,363, filed on Nov. 5, 2008.

(51) Int. Cl.
| | | |
|---|---|---|
| *A61B 19/00* | (2006.01) | |
| *G01L 5/00* | (2006.01) | |
| *A61B 5/00* | (2006.01) | |
| *A61B 5/103* | (2006.01) | |

(52) U.S. Cl.
CPC ............... *G01L 5/0038* (2013.01); *A61B 5/00* (2013.01); *A61B 5/103* (2013.01); *A61B 5/7275* (2013.01); *A61B 2560/0418* (2013.01); *A61B 2562/0247* (2013.01); *A61B 2562/046* (2013.01)
USPC ............................ 600/557; 600/553; 600/587

(58) Field of Classification Search
USPC .................... 600/300, 587–595, 553, 557; 73/65.01–65.09, 489–490, 492, 597; 324/160; 702/144, 160, 176, 182
See application file for complete search history.

(56) References Cited

U.S. PATENT DOCUMENTS

| | | | | |
|---|---|---|---|---|
| 2,422,520 | A * | 6/1947 | Bartley | 600/557 |
| 2,704,539 | A | 3/1955 | Fisher | |
| 4,467,815 | A * | 8/1984 | O'Brien et al. | 600/553 |
| 4,641,661 | A | 2/1987 | Kalarickal | |
| 5,002,065 | A * | 3/1991 | LaCourse et al. | 600/552 |
| 5,195,532 | A * | 3/1993 | Schumacher et al. | 600/552 |
| 5,433,211 | A * | 7/1995 | Brammer et al. | 600/552 |
| 5,578,766 | A | 11/1996 | Kondo | |
| 5,592,947 | A | 1/1997 | Lavigne | |
| 5,941,835 | A * | 8/1999 | Sundman | 600/592 |
| 6,041,667 | A | 3/2000 | Pischinger et al. | |

(Continued)

FOREIGN PATENT DOCUMENTS

| | | |
|---|---|---|
| EP | 1078624 | 2/2001 |
| EP | 1800644 | 6/2007 |

(Continued)

OTHER PUBLICATIONS

GB Search Report for corresponding application No. GB0820253.3 dated Nov. 19, 2010.

(Continued)

*Primary Examiner* — Rene Towa
(74) *Attorney, Agent, or Firm* — Renner, Otto, Boisselle & Sklar, LLP

(57) ABSTRACT

A force transducer comprises a handle operably connected to a probe having an elongate tip. The force transducer includes a biasing element arranged with respect to the handle, in force transmitting communication with the probe, and a detector operable to detect a degree of force applied between the probe and the handle. The force transducer further includes an actuator operable to exert a force on the biasing element in dependence upon the degree of force detected by the detector so as to cause a predetermined force to be transmitted from the handle to the probe.

15 Claims, 22 Drawing Sheets

(56) References Cited

U.S. PATENT DOCUMENTS

| | | | |
|---|---|---|---|
| 6,063,044 A | 5/2000 | Leonard | |
| 6,190,334 B1* | 2/2001 | Lasky et al. | 600/587 |
| 6,196,976 B1* | 3/2001 | Christy | 600/557 |
| 2004/0173220 A1* | 9/2004 | Harry et al. | 128/892 |
| 2005/0124910 A1* | 6/2005 | Gupta | 600/552 |
| 2006/0047315 A1 | 3/2006 | Colloca et al. | |
| 2008/0071188 A1 | 3/2008 | Horne et al. | |
| 2009/0270775 A1* | 10/2009 | Tommerdahl et al. | 601/70 |
| 2010/0198022 A1* | 8/2010 | Vuillerme et al. | 600/301 |

FOREIGN PATENT DOCUMENTS

| | | |
|---|---|---|
| JP | 55004548 | 6/1978 |
| JP | 06327745 | 5/1993 |
| JP | 2001231840 | 2/2000 |
| JP | 2006181304 | 7/2006 |
| KR | 030018654 | 8/2001 |
| KR | 060104342 | 3/2005 |
| WO | 97/18450 | 5/1997 |
| WO | 99/05965 | 2/1999 |
| WO | 01/43638 | 1/2001 |
| WO | 2006/100331 | 9/2006 |
| WO | 2007/023637 | 3/2007 |
| WO | 2007/059971 | 5/2007 |
| WO | 2009/070325 | 6/2009 |
| WO | 2009/144622 | 12/2009 |
| WO | 2010/024492 | 3/2010 |

OTHER PUBLICATIONS

GB Search Report for corresponding application No. GB0820253.3 dated Jun. 1, 2009.

GB Search Report for corresponding application No. GB0820253.3 dated Apr. 21, 2009.

* cited by examiner

FORCE TRANSDUCER, MEDICAL INSTRUMENT, AND MACHINE IMPLEMENTED METHOD

This application claims priority to U.S. Provisional Application No. 61/111,363 filed on Nov. 5, 2008 in which is hereby incorporated herein by reference in its entirety.

BACKGROUND OF THE INVENTION

1. Field of the Invention

The present invention relates to a force transducer, medical instrument, and machine implemented method.

2. Description of the Prior Art

Diabetes mellitus is a chronic illness with a prevalence approaching 8% in most developed countries. Throughout Europe, there are approximately 27 million registered diabetic individuals; the majority (greater than 80%) of these individuals are presenting Type 2 diabetes. From a UK perspective, the King's Fund has estimated the economic implications of diabetes to reside at £2 billion annually. Moreover, the management of diabetes and its associated complications are set to demand 10% of the total National Health Service (NHS) budget by 2011.

Diabetic peripheral neuropathy is a frequent complication of diabetes mellitus. Its prevalence has been observed to vary between studies, but around 60% of all Type 2 diabetic individuals will eventually develop this condition within the first 10 years of being diagnosed with diabetes. The condition tends to follow a distal to proximal pattern of distribution through the body; hence the toes are often the first areas to exhibit neurological impairment. As such, peripheral sensory neuropathy is regarded as a key factor for the development of ulceration in the diabetic foot.

Research has maintained that an inability to detect a 10 g-force (i.e. 98 mN) applied at key weight bearing sites is a sufficiently capable measurement for neuropathy and, thereby, is consistent with an increased risk of plantar ulceration.

FIG. 1 shows a schematic view of a prior art monofilament testing device 101 for testing for the presence of diabetic peripheral neuropathy in patients. A monofilament 103 is formed of extruded homopolymer, typically polyamide, retained within or fixed to a handle 102. The extruded homopolymer monofilament 103 is fixed at one end (i.e. at the handle 102), allowing for it to be deflected when an axial force is applied to the opposite end. The extruded homopolymer monofilament is used to impart a prescribed force, which is defined by a specified lateral deflection, or buckling, under the associated load.

FIG. 2 shows the monofilament device 102 with an applied axial 10 g-force (i.e. 98 mN) 105, resulting in lateral deflection of the monofilament 104 by bending of 10 mm. The test is typically conducted discreetly, whereby clinicians are required to apply the monofilament at 90° to the target site (one of the key weight points) and observe a 10 mm deflection, thereby applying a 10 g-force (i.e. 98 mN) and noting any patient response.

However, given the apparent variability in fibre length and diameter of the monofilament, in addition to the differences in crystalline structure between grades of polyamide and above all, the material's susceptibility to changes in humidity (hydroscopic changes), the nominal mechanical properties are rapidly compromised during use.

FIG. 3 shows a plot of the mean buckling force $f_B$ in gram-force (i.e. units of 9.8 mN) against the number of compressions N of four commercially available '10 g-force load' monofilaments from the vendors: Bailey, Mumford, North Coast and Timesco. The illustrated test results show that all of these devices show a reduction in the force needed to achieve the 10 mm lateral deflection each time the device is used, with significant changes occurring over the course of 10 uses.

SUMMARY OF THE INVENTION

An object of the present invention is to provide an improved force transducer, medical instrument and machine implemented method.

In a first aspect, there is provided a force transducer comprising: a handle operably connected to a probe having an elongate tip; a biasing element arranged with respect to the handle, in force transmitting communication with the probe; a detector operable to detect a degree of force applied between the probe and the handle; and an actuator operable to exert a force on the biasing element in dependence upon the degree of force detected by the detector so as to cause a predetermined force to be transmitted from the handle to the probe.

Therefore, by using an actuator operable to cause a predetermined force to be applied between the handle and the probe in dependence upon detected force applied between the handle and the probe (e.g. by a clinician applying the probe to a target site), reproducibility of target force can be improved. Additionally, any degree of subjectivity in applying a desired force to a target area is reduced, thus improving the accuracy of testing for diabetic peripheral neuropathy. Furthermore, the force transducer can easily be used by a patient for self-monitoring.

In a second aspect, there is provided a medical instrument comprising: a force transducer operable to apply a predetermined force at a position selected from an array of predetermined possible positions as a stimulus to a test area of a body part of a patient; a detector operable to detect a location of the test area of the body part with respect to a current position of the force transducer and the array of predetermined possible positions; and a translation element operable to move the force transducer to one or more positions in the array closest to the location of the test area as detected by the detector. The force transducer can be a force transducer in accordance with the first aspect of the invention.

Accordingly, the medical instrument may be used to carry out automated testing by applying a predetermined force to different target sites (test areas), thus allowing a patient to self-monitor for any degree of sensory neuropathy on a regular basis.

In a third aspect, there is provided a machine implemented method of detecting an increased risk of diabetic neuropathic ulceration using a force transducer operable to apply a predetermined force to a test area of a body part of a patient, the method comprising: detecting a location of the test area with respect to a position of the force transducer; moving the force transducer to the location of the test area; applying a predetermined force to the test area using the force transducer; and recording whether a response is received from the patient regarding touch sensation at the test area.

Accordingly, automated testing by applying a predetermined force to different target sites (test areas) may be carried out thus allowing a patient to self-monitor for any degree of neuropathy on a regular basis. The force transducer can be a force transducer according to the first aspect of the invention. The machine implemented method can be carried out using said instrument according to the second aspect of the invention.

The invention also relates to use of a force transducer according to the first aspect of the invention in detection of an increased risk of diabetic neuropathic ulceration.

The invention further relates to use of a medical instrument according to the second aspect of the invention in detection of an increased risk of diabetic neuropathic ulceration.

Further aspects and respective features of the invention are defined in the appended claims.

BRIEF DESCRIPTION OF THE DRAWINGS

The above and other objects, features and advantages of the invention will be apparent from the following detailed description of illustrative embodiments which is to be read in connection with the accompanying drawings, in which.

DESCRIPTION OF THE PREFERRED EMBODIMENTS

A force transducer, medical instrument, and method are disclosed. In the following description, a number of specific details are presented in order to provide a thorough understanding of embodiments of the present invention. It will be apparent however to a person skilled in the art that these specific details need not be employed to practise the present invention. Conversely, specific details known to the person skilled in the art are omitted for the purposes of clarity in presenting the embodiments.

Figure 1:
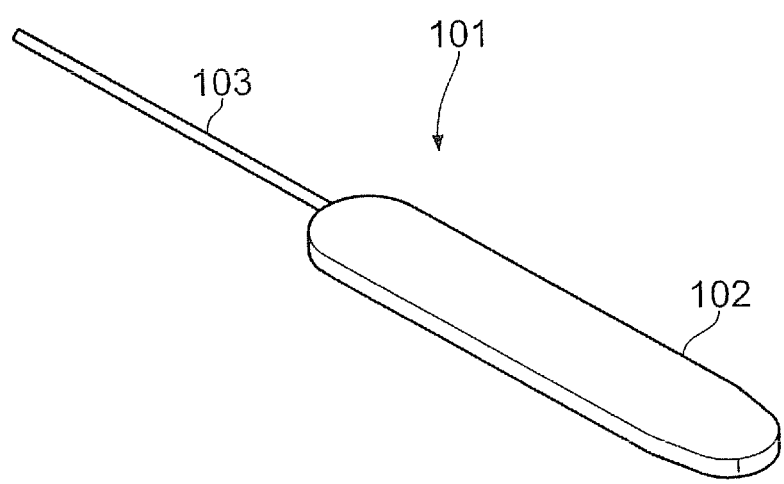
FIG. 1 shows a prior art monofilament testing device for testing for the presence of diabetic peripheral neuropathy in patients.
Figure 2:
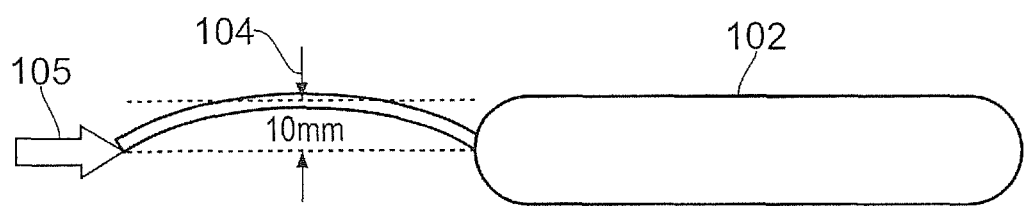
FIG. 2 shows a prior art monofilament with an applied 10 g-force load with a deflection of 10 mm.
Figure 3:
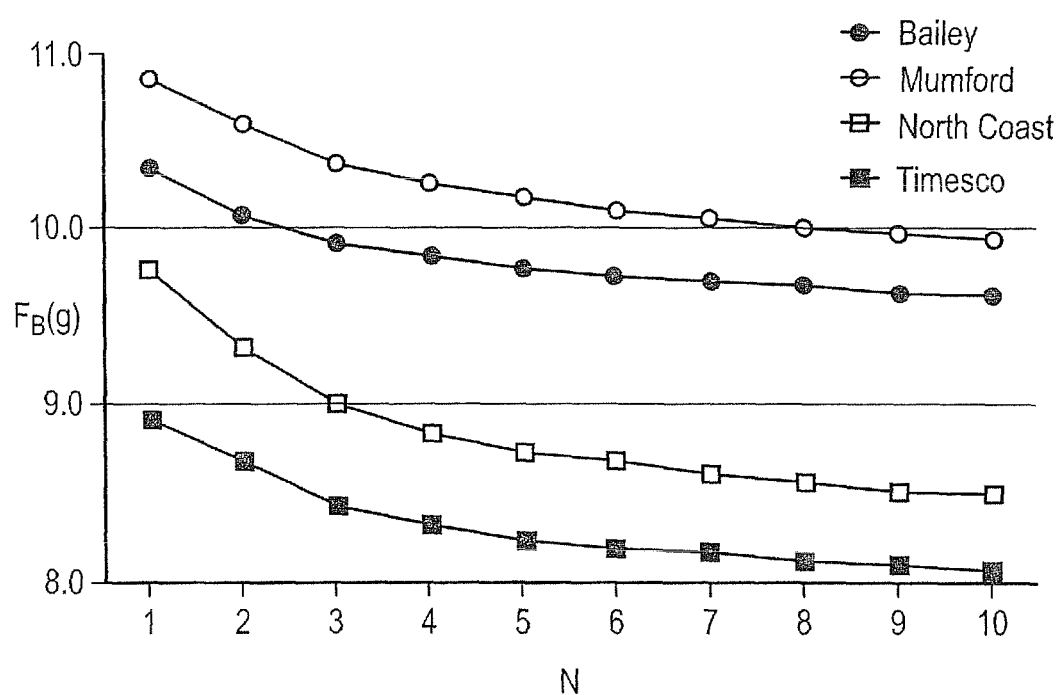
FIG. 3 shows a plot of the mean buckling force in g-force (i.e. 10 mN) against the number of compressions of four commercially available prior art "10 g-force load" monofilaments.
Figure 4:
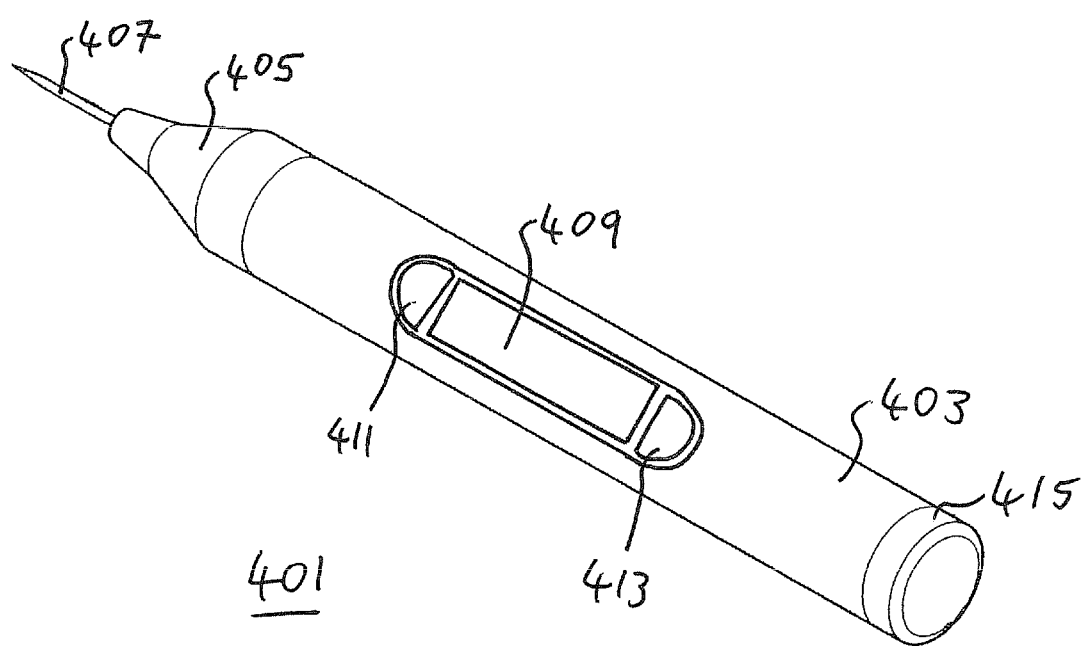
FIG. 4 shows a schematic perspective view of a force transducer according to an embodiment of the present invention.

FIG. 4 shows a force transducer 401 according to an embodiment of the present invention. The force transducer 401 comprises a housing for 403, attached to which is a nose 405 which contains a probe 407. The force transducer 401 additionally comprises a display 409 for displaying information to a user, along with an input button 411 and an input button 413 which allow a user to control functions of the force transducer 401. An end cap 415 is attached to an opposite end of the housing 403 from the nose 405. The end cap 415 is detachable from the housing 403 so as to allow a user to, for example, change a battery used to power the force transducer 401. The housing allows a user to hold the force transducer and therefore acts as a handle of the force transducer. In other words, at least in some embodiments, the handle is the housing 403 of the force transducer 401.

Figure 5:
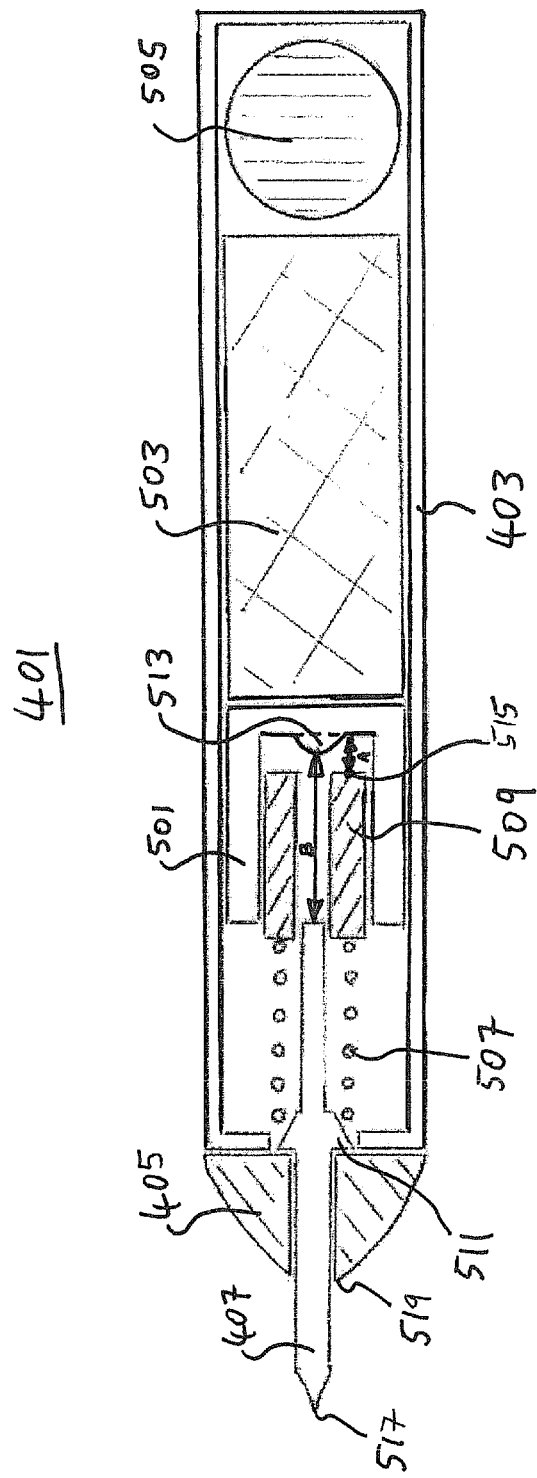
FIG. 5 shows a schematic cross-sectional view of a force transducer according to an embodiment of the invention shown in FIG. 4.

FIG. 5 shows a cross-sectional view of the force transducer 401. The housing 403 contains an actuator and sensor module 501, a printed circuit board (PCB) 503, and a power to source 505. The nose 405 comprises an aperture through which the probe 407 may move. Additionally, the probe 407 is biased towards the nose 405 by a compression spring 507 (illustrated in schematic cross-section by the small circles in FIG. 5). In other words, an end of the probe 407 which is outside the housing 403 and the nose 405 (a tip 517 of the probe) is biased by the compression spring 507 away from the nose 405 and the housing 403. The actuator and sensor module 501 is operable to drive an actuator piston 509 axially within the housing 403 such that the compression spring 507 can be compressed and/or displaced with respect to the probe 407.

The probe 407 comprises a flange 511 which is in force transmitting communication with the compression spring 507. Additionally, in embodiments of the present invention, the flange 511 has a diameter which is larger than the aperture in the nose 405 through which the probe 407 may move. Therefore, although the tip 517 of the probe 407 is biased away from the housing 403 by the compression spring 507, the probe 407 is retained such that is cannot come completely out of the nose 405 because the nose 405 acts as a hard-stop, i.e. an abutment, when brought into contact with the flange 511.

Preferably, the compression spring is precision wound and acts as a biasing element. However, it will be appreciated that other suitable biasing elements could be used.

The actuator and sensor module 501 comprises a sensor 513 operable to detect a relative distance between the actuator and sensor module 501 and the actuator piston 509. The sensor 513 is also operable to detect a relative distance between the actuator and sensor module 501 and the probe 407. For example, the sensor 513 can measure a distance from the sensor 513 to an end 515 of the actuator piston 509 (indicated as distance 'A' in FIG. 5). Additionally, the sensor 513 is operable to measure a distance 'B' between the sensor 513 and an end of the probe 407 which is an opposite end of the probe 407 to the tip 517 of the probe. The actuator and sensor module 501 is in electrical connection with the printed circuit board 503, which is powered by the power source 505. The printed circuit board 503 will be described in more detail later below.

In the embodiment shown in FIG. 5, the probe 407 is operable to move axially through the aperture in the nose 405 with respective to the nose 405 and the housing 403. When the force transducer 401 is not in use, the probe 407 extends from the nose 405 to an extent determined by a position of the flange 511 along the length of the probe 407, and the dimensions of the nose 405. Additionally, the aperture in the nose 405 through which the probe 407 passes provides a surface which may act as a bearing so as to facilitate movement of the probe 407 with respect to the nose 405. That is to say, the material forming the aperture acts as a bearing for the probe 407.

It will be appreciated that foreign material could potentially foul the motion of the probe 407 with respect to the nose 405 and the housing 403 so increasing friction and affecting force delivered to the probe. For example, foreign material may be present or be introduced between an outer surface of the probe 407 and a surface of the nose 405 which forms the aperture in the nose 405. Therefore, in an embodiment, the probe shaft is fluted so as to reduce the contact area between the probe 407 and the nose 405. Alternatively, a lip seal between the nose 405 and the probe 407 may be used, although it will be appreciated that any other suitable method of inhibiting entry of foreign material into the force transducer may be used.

In embodiments of the present invention, the probe 407 is made of one piece of extruded polymer in the form of a monofilament. However, in other embodiments, the probe can be manufactured from two pieces, which may be removably attached to each other, thus enabling the tip to be changed and improving hygiene. Additionally, the nose 405 may be removably attached to the housing 403 using a suitable screw thread fitting or bayonet fitting although it will be appreciated that other suitable fittings may be used. This enables the probe to be removed and replaced with a new and/or different probe. This improves hygiene and allows the probe to be changed if it becomes damaged, as well as allowing different shaped probes having different tip profiles to be used.

The dimensions of the probe 407, the compression spring 507, the actuator piston 509, and the actuator and sensor module 501 are such that an exposed portion of the probe 407 may be pushed all the way into the nose 405 so that the probe is under-flush with a nose end surface 519, thus reducing the potential for so-called needle-stick injury.

In another embodiment, the probe 407 is typically manufactured from polycarbonate of suitable medical grade, due to its mechanical stability and resistance to bacterial growth. Alternatively, semi-crystalline materials, such as polyphenylene sulphide (PPS) or polyetheretherketone (PEEK) could also be used due to their well known structural integrity and inherent lubricity.

The housing 403, nose 405, and end cap 415 are typically manufactured from medical grade styrenes, for example acrylonitrile butadiene styrene (ABS), as these typically have a high surface finish, are impact resistant, and are geometrically stable. Additionally, it will be appreciated that the housing 403, nose 405, and end cap 415 could be pigmented or painted with a suitable decorative finish. Preferably, the housing 403 comprises two injection moulded pieces which may be snap-fitted together so as to form the housing 403. This facilitates ease of assembly. Additionally, it will be appreciated that other materials may be used to manufacture the housing, nose 405, and end cap 415 such as brushed aluminium or stainless steel, although any other suitable material could be used.

It will be appreciated that the geometry of the force transducer 401 is largely determined by components and devices contained within. However, the force transducer 401 should typically meet the demands of the market in respect of appearance and ergonomic features.

In use, the probe 407 may be applied to a test area on a body part of a patient so that the probe 407 is displaced with respect to the housing 403. This compresses the compression spring 507 against the actuator piston 509. By detecting the relative displacement of the probe 407 with respect to the sensor 513 and the displacement of the actuator piston 509 with respect to the sensor 513, the relative compression of the compression spring 507 may be determined, thereby allowing the force which is exerted on the probe by the actuator piston 509 to be calculated. This will be described in more detail below.

When an axial force is applied to the probe 407 (for example by pressing the probe 407 against a test area on a patient's foot), the axial force is translated to the compression spring 507 because the compression spring 507 is in force transmitting communication with the probe 407 at the flange 511 as shown in FIG. 5. The sensor 513 detects the relative displacement of the probe 511 with respect to the sensor 513 and displacement of the actuator piston 509 with respect to the sensor 513 (i.e. the compression of the spring 507) and sends a signal indicative of these values to the PCB 503. The PCB 503 can then determine a degree of compression of the compression spring 507 and thus generate a force value indicative of a force being applied to the probe 407 because the spring obeys a known adapted form of Hooke's Law. The force value generated by the PCB 503 can then be displayed on the display 409.

In embodiments of the invention, the sensor 513 is operable to measure the displacement of the probe 407 with respect to the sensor and the displacement of the actuator piston with respect to the sensor using optical encoding. However, it will be appreciated that other suitable methods such as Hall effect measurement, magnetic field disruption (eddy current detection), magnetic field inductance (such as used in linear variable differential transformers), and the like could be used.

In the embodiment described above, the actuator piston 509 makes mechanical contact with the actuator and sensor module 501 thus forming an end stop for motion of the actuator piston 509. In some embodiments, the actuator piston 509 may be used to compress the compression spring 507 so as to cause a predetermined force to be transmitted from the actuator piston 509 to the probe 407 via the compression spring

507. This will be described in more detail later below. This method of operation is referred to as active force application, whereas a situation in which the actuator piston 509 acts as an end stop for motion of the compression spring 507 is referred to as passive force application. Both of these will be described in more detail later below.

Circuitry used in the force transducer described with respect to FIG. 5 above will now be described with reference to FIG. 6.

Figure 6:
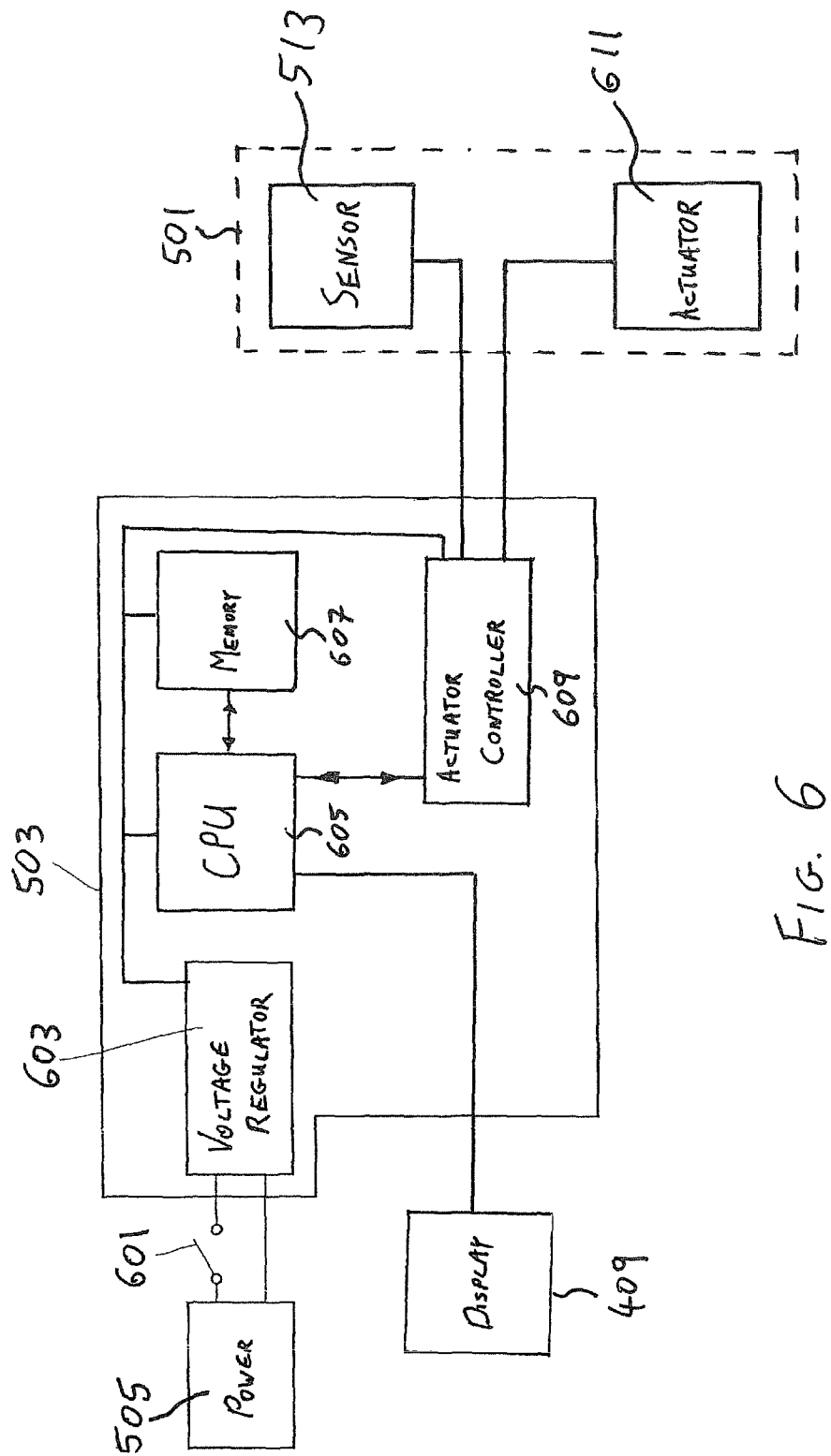
FIG. 6 shows a schematic view of circuitry associated with the force transducer of FIG. 4.

FIG. 6 shows a circuit diagram of an electrical system used in embodiments of the force transducer described above. In particular, the electrical system comprises the power source 505, a main power switch 601, the printed circuit board 503, the actuator and sensor module 501 (indicated by the dashed line), and the display 409. The printed circuit board 503 comprises a voltage regulator 603, a central processing unit (CPU) 605, a memory 607, and an actuator controller 609. The CPU 605, memory 607 and actuator controller 609 receive power from the power source 505 via the voltage regulator 603. The voltage regulator 603 is also operable to provide power to the actuator and sensor module 501 and to the display 409. The printed circuit board 503 is also electrically connected to the display 409 and the input buttons 411 and 413.

The CPU 605 is operable to communicate with the memory 607, the actuator controller 609, and the display 409 and controls the main operation of the force transducer 401. The actuator controller 609 is operable to communicate with the sensor 513 and an actuator 611 associated with the actuator and sensor module 501. The actuator 611 is operable to control motion of the actuator piston 509 within the actuator and sensor module 501. In the embodiment shown in FIG. 5, the actuator 611 is operable to control electromechanically the motion of the actuator piston 509. However, it will be appreciated that other suitable forms of motion control may be employed such as a gear system driven by a suitable electric motor. In other words, the actuator piston 509 together with the actuator and sensor module 501 form a linear actuator. However, in other embodiments, the actuator piston 509 together with the actuator and sensor module 501 form a rotary to linear actuator, although it will be appreciated that any other suitable actuator could be used.

The power source 505 is typically a lithium ion cell with an operating voltage of 3.3 volts. However it will be appreciated that any other suitable alternative power source may be used.

As mentioned above, the force transducer 401 may operate in a passive mode in which the force transducer detects a force which is applied to the probe 407 by contacting the probe 407 against a test area of a body part of a patient. For example, the force transducer 401 may be positioned with respect to a patient's foot such that the probe 407 is pressed against a selected weight bearing site on a plantar surface of the patient's foot. The force transducer 401 then detects the amount of force that is being applied to the test area by the probe 407 by detecting the displacement of the probe 407 within the housing 403 using the sensor 513. The probe 407 is arranged with respect to the actuator piston 509 and the compression spring 507 such that motion of the probe 407 remains within the linear range of the compression spring 507 (i.e. the compression spring remains in a regime which obeys Hooke's Law). Therefore, the CPU 605 can generate the force value from compression of the spring as indicated by the detected displacement values.

In embodiments of the invention, the CPU 605 is operable to control the display 409 to indicate a level of force which is applied to the probe 407. Additionally, the CPU 605 is operable to control the display 409 so as to indicate when the level of force applied to the probe 407 is greater than a "pressure" threshold or whether the force is greater than an "over-pressure" threshold.

Figure 7:
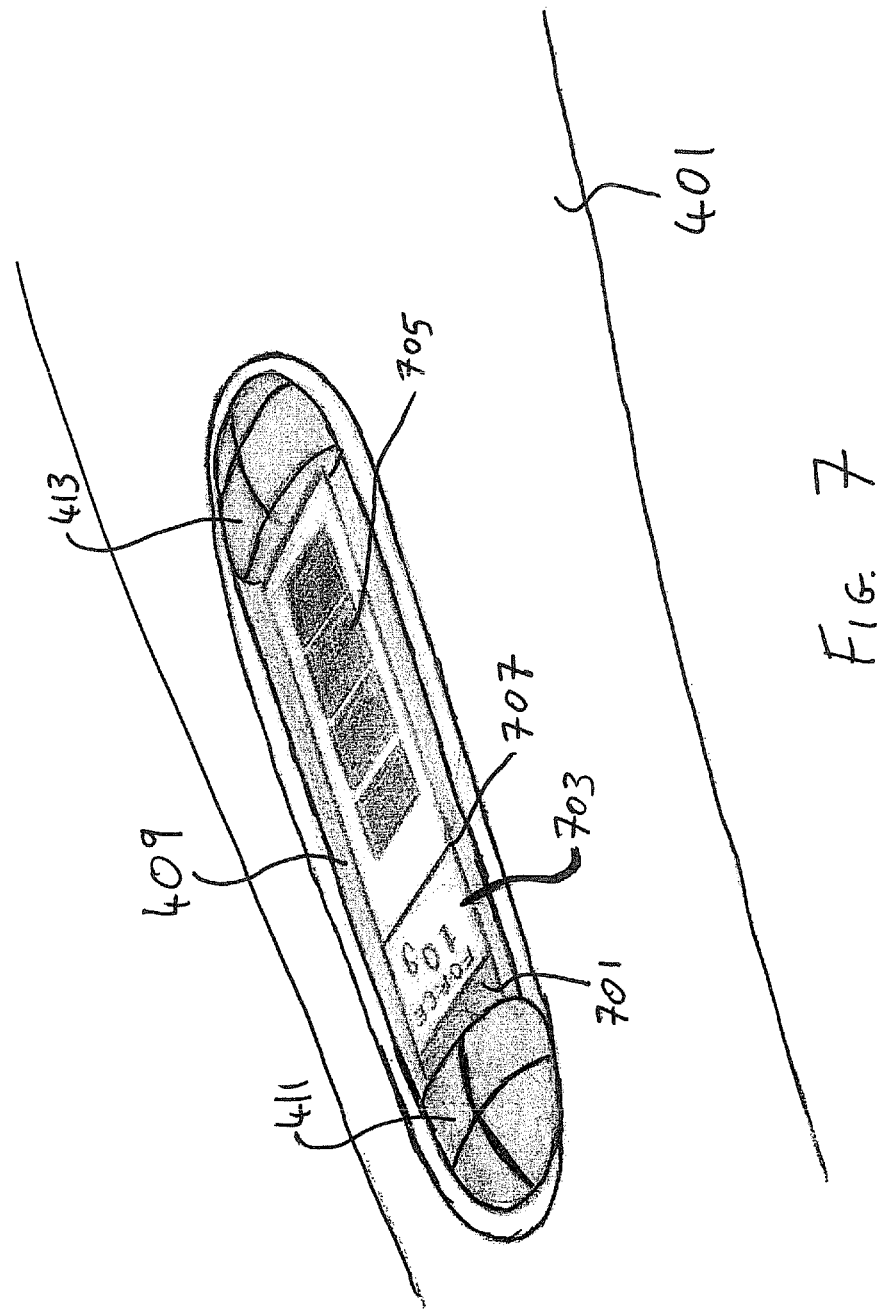
FIG. 7 shows a schematic view of a display and user controls associated with the force transducer of FIG. 4.

The display 409 used in embodiments of the present invention is illustrated with respect to FIG. 7.

FIG. 7 shows the display 409 together with the input buttons 411 and 413. The display 409 comprises a plurality of regions which indicate different operational aspects of the force transducer 401. In the embodiment shown in FIG. 7, the display 409 comprises a bi-colour light emitting diode (LED) 701, a force display area 703 for displaying the amount of force applied to the probe 407, a bar chart indicator 705 and a threshold marker 707. The threshold marker 707 together with the bar chart indicator 705 comprise a display region which allows a user to ascertain what proportion of the threshold is currently being applied to the probe 407. In other words, the threshold marker 707 corresponds to a point at which the force applied to the probe equals the pressure threshold, and the bar chart indicator 705 indicates the force which is being applied to the probe 407 as a percentage of the pressure threshold.

In order to detect whether the force applied to the probe 407 is greater than the pressure threshold and the over-pressure threshold, the CPU 605 is operable to receive data from the sensor 513 via the actuator controller 609 which relates to the relative displacements of the actuator piston 509 and the probe 407 with respect to the sensor 513. The CPU 605 then generates the force value by comparing the relative displacement values to values stored in a lookup table (LUT) in the memory 607. The values stored in the LUT relate the relative displacements of the actuator piston 509 and the probe 407 to the amount of force applied to the probe 407 in dependence upon the spring constant of the compression spring 507 according to Hooke's Law.

However, it will be appreciated that the system used in the force transducer 401 is a non-ideal system and therefore the simplistic view of Hooke's Law where f=kx (where f is the force applied to the compression spring 507, k is the spring constant of the compression spring 507, and x is the extension of the compression spring 507 with respect to a natural length of the compression spring 507) is unlikely to apply. In other words, the force applied to the compression spring is proportional to the extension/compression of the spring. Therefore, the look-up table stored in the memory 607 can be used to store appropriate values which have been calculated to take account of frictional losses in the system as well as non-ideal motions of the spring and other deviations from the simple model provided by Hooke's Law.

The CPU 605 then compares the generated force value with the pressure threshold value and the over-pressure threshold value to detect whether the generated force value is greater than these values. In the embodiments described with reference to FIGS. 4 to 7, the pressure threshold equates to a 98 mN load (i.e. 10 g-force), although it will be appreciated that any other suitable pressure threshold could be used. Typically, the over-pressure threshold is 30% more than the pressure threshold although it will be appreciated that could be any suitable percentage or value for the over-pressure threshold could be used.

As mentioned above, the CPU 605 compares the generated force value with the pressure threshold value and the over-pressure threshold value. If the generated force value is less than the pressure threshold value, then the CPU 605 is operable to cause the bicolour LED 701 not to illuminate. However, if the generated force value is greater than the pressure threshold value, but less than the over-pressure threshold value, then the CPU 605 is operable to cause the bicolour LED 701 to illuminate as green, thus indicating that the threshold force has been attained. However, if the CPU 605 detects that the generated force value is greater than the over-pressure threshold value, then the CPU 605 is operable to cause the bicolour LED 701 to illuminate as red, thus indicating to the user that too much force has been applied to the probe 407 and that the test is therefore invalid.

However, it will be appreciated that the force transducer may be used by diabetic individuals for self-testing. Because this may involve testing areas of the body which are out of sight, for self-testing a non-visual indicator could be used instead of, or as well as, a visual indication as provided by the display.

For example, a tactile indicator in the form of a vibrating element could be used, where the vibrations would be sensed through the housing by the person holding the device. For example, the vibrating element could be caused to cause vibrations in place of, or as well as, the above-described green. For the case of overload, the red light indicator could be substituted with vibration at a different frequency, e.g. higher frequency. This might also be useful for conventional testing by clinical staff. If desired, the device could be switchable between tactile and visual indication outputs.

Another alternative to visual indication is audible indication. An audible indicator could be provided to emit a tone in place of, or as well as, the above-described green light. For the case of overload, the red light indicator could be substituted with emission of a tone of different audible frequency, e.g. higher frequency.

During operation in which the force transducer 401 in the passive mode, the CPU 605 is also operable to control the force display area 703 to display the amount of force that is being applied to the probe 407 as well as being operable to control the bar chart indicator 705 and the threshold marker so as to indicate a proportion of the threshold force which is currently being applied to the probe 407. This enables a user to apply the force probe to a test area so as to provide a predetermined force in a controlled manner, thus simplifying testing for diabetic neuropathy.

In an embodiment, the user may set the value of the pressure threshold value and the over-pressure threshold value by manipulating the input buttons 411 and 413 in a suitable fashion. The CPU 605 is then operable to control the display 409 so as to alter the position of the threshold marker 707 and/or control operation of the bar chart indicator 705 accordingly. Additionally, the user can control power to the force transducer 401 by, for example, pressing the input button 411 and 413 simultaneously for greater than a predetermined number of seconds thus indicating to the CPU 605 that the device (force transducer 401) should be switched off or on as appropriate. Alternatively, the input button 411 can be used to control operation of the power switch 601 whilst the input button 413 can be used to control other functions of the force transducer 401. However, it will be appreciated that any other suitable input method to control the power switch 601 could be used.

Figure 8:
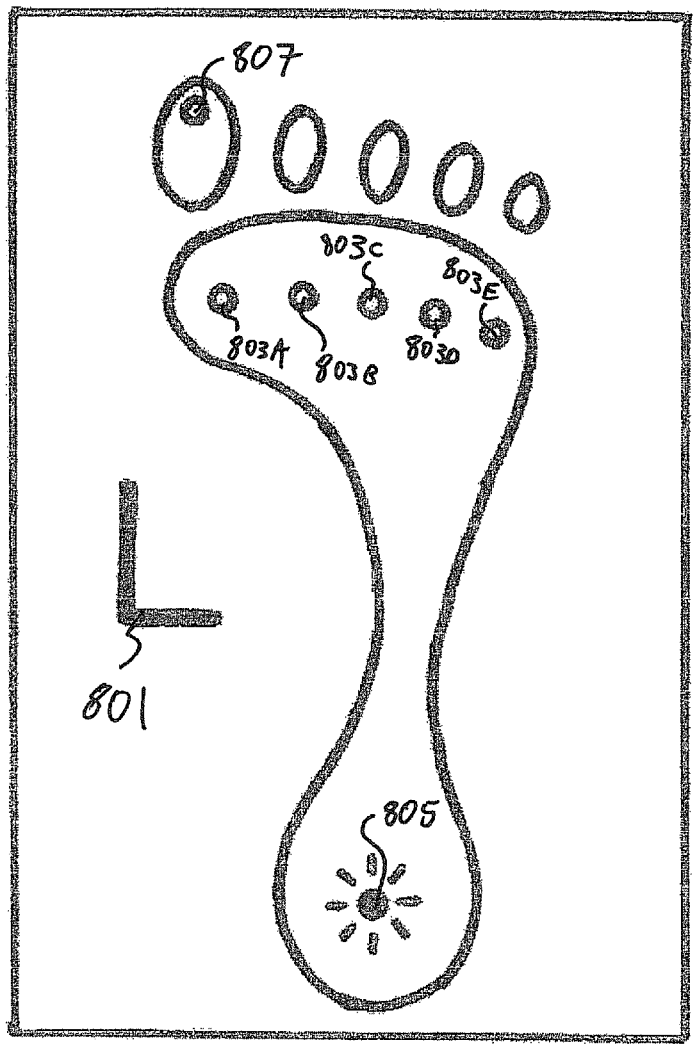
FIG. 8 is a schematic view of a display in accordance with an embodiment of the present invention for indicating to a user a position at which the force transducer should be applied to a body part.

In some embodiments, the display 409 comprises a display region as illustrated in FIG. 8 which shows a display indicator for indicating to a user to which part of a patient's foot the probe should be applied in order to carry out a diabetic neuropathy test.

FIG. 8 shows a display region for indicating to a user test areas to which the probe 407 should be applied. In FIG. 8, the display region comprises a limb indicator 801 for indicating whether a left or right side of the patient should be tested. For example, in the embodiment shown in FIG. 8, the limb indicator 801 shows an indication "L" indicating that a left limb of the patient should be used during the test. If the limb indicator region 801 shows an "R" then this indicates to a user that the test should be applied to a patient's right limb (e.g. right foot). Additionally, the display region shown in FIG. 8 comprises a region indicative to the type of limb to which the test areas correspond. For example, test areas 803a, 803b, 803c, 803d, and 803e correspond to the first to fifth metatarsophalangeal joint of the patient's left foot respectively. A test area 805 corresponds to the calcaneum (heel) of the patient's left foot, and a test area 807 corresponding to the hallux (tip of big toe) of the patient's left foot. In operation, the CPU 605 can control the display 409 to illuminate or otherwise indicate which test area should be tested with the force transducer 401. For example, as shown in FIG. 8, the test area 805 is schematically shown as illuminated, thus indicating to a user that the probe should be applied to the calcaneum of the patient's left foot. The test procedure will be described in more detail later below.

As described above, the force transducer 401 may also be used in an active mode in which the actuator piston together with the actuator and sensor module 501 can cause the compression spring 507 to be displaced with respect to the probe 407 so as to cause a predetermined force to be transmitted from the actuator piston 509 to the probe 407.

As mentioned above, the probe 407 is biased towards the nose 405 (i.e. the tip 517 of the probe 407 is biased away from the nose 405) by the compression spring 507. This has an advantage that the probe 407 may be retained with nose 405 and the force transducer 401 may be operated without being unduly influenced by gravity. The overall force on the probe 407 $f_{net}$ may be calculated according to:

$$f_{net}=f_{const}+kx \qquad \text{equation 1}$$

where $f_{const}$ is dependent upon the mass of the probe 407 (via static and kinetic friction between the probe and the nose), the preload of the compression spring 507, and the inertial and frictional losses in the system. Here, preload is taken to mean a force required to bias the probe flange 511 against the nose 405 without any load being applied to the tip 517 of the probe 407. As described above, k is the spring constant of the compression spring 507 and x is the displacement from an initial position of the compression spring 507 when the flange 511 is biased against the nose (a preload position).

In the embodiment described with reference to FIGS. 4 to 8, the spring constant of the compression spring 507 is 4.9 mN/mm (0.5 g/mm), the mass of the probe 407 is 2 grams, inertial and frictional losses are 4.9 mN (0.5 g), and preload of the compression spring 507 is 29.4 mN (3 g). In other words, $f_{const}$=34.3 mN (3.5 g) Therefore, in order to move the probe 407 from the position at which the flange 511 is biased against the nose 405, a force greater than 34.3 mN (3.5 g) needs to be applied to the probe 407.

In the active mode, to operate the force transducer, a user can apply the probe 407 to a test area and move the housing 403 with respect to the test area so as to cause the probe to be displaced inwards with respect to the nose 405 and the housing 403. The probe is thus moved from a static bias position or resting position. The CPU 605 then detects, in dependence upon signals received from the sensor 513, a relative displacement of the probe 407 and the actuator piston 509 with respect to the sensor 513 (i.e. the compression of the spring) so as to calculate an applied force 407. The CPU 605 then generates a control signal indicative of an amount by which the actuator piston should be moved towards the nose 405 so as to cause a predetermined force to be applied from the housing 403 to the probe 407. The control signal is sent from the CPU 605 to the actuator and sensor module 501 via the actuator controller 609.

For example, if the probe is displaced axially with respect to the nose 405 and the housing 403 by 3 mm, then the force applied to the probe 407 is 49 mN (5 g). Therefore, in order to apply a target force of, for example, 98 mN (10 g) to the probe 407, the CPU 605 generates a control signal so as to cause the actuator piston 509 to move towards the nose 405 by 10 mm (i.e. 10 mm×4.9 mN/mm=49 mN (5 g)) according to equation 1 above i.e. to further compress the spring by 10 mm.

Typically, in embodiments of the present invention, the CPU 605 is operable to detect the displacement of the probe 407 with respect to the nose 405 and thus detect the force to be applied to the compression spring 507 using the actuator piston 509 within 250 milliseconds of the probe being moved from the static position. The CPU 605 then sends control signals to the actuator 611 via that actuator controller 609 so as to cause the actuator piston 509 to move to the appropriate distance to apply the predetermined force to the probe 407 within 1.5 seconds of the probe being moved from the static position. However, it will be appreciated that any other times suitable for applying force to the probe 407 may be used.

In operation, a user may select a target force (threshold force) using the user input buttons 411 and 413. Typically, target forces of 6 g, 8 g, and 10 g can be selected although it will be appreciated that any other suitable target force could be used.

The CPU 605 then causes the display 409 to indicate to the user a test site to which the probe 407 should be applied, for example as described above with reference to FIG. 8. The order in which test sites are selected may be randomly generated by the CPU 605 or it may be preset and stored within the memory 607 according to appropriate clinical protocols.

The user may then apply the tip of the probe 407 to the test area indicated by the display 409 and cause the probe 407 to be displaced slightly inwards from the static position (flange 511 in physical contact with the nose 405) so as to displace the flange 511 away from the nose 405.

Then, as mentioned above, the CPU 605 generates an appropriate control signal in dependence upon the detected spring compression so as to cause the actuator piston 509 to compress the compression spring 507 by a suitable amount thus causing the predetermined force to be applied to the probe 407.

Once the predetermined force has been applied to the probe 407, the CPU 605 causes the display 409 to illuminate the bicolour LED 701 green to indicate that the predetermined force has been applied. In an embodiment, an audible signal or a tactile signal may also be provided so as to indicate that the predetermined force has been applied between the probe 407 and the housing.

The CPU 605 can then cause the display 409 to request from the user an indication, made via a suitable input button 411 or 413, indicating that the patient felt the stimuli provided by the probe 407. The CPU 605 then causes the memory 607 to store a record of the outcome of the test (i.e. positive/negative response against the location of the test area as indicated by the display 409 with reference to FIG. 8) so as to generate a correlation log. Once the CPU 605 has stored this result to the memory 607, a second site will be selected by the CPU 605 and displayed to the user on the display 409 as described above with reference to FIG. 8. The process is then continued until a predetermined number of test areas (test sites) have been selected, tested and the results stored in the correlation log in the memory 607.

In an embodiment, the force transducer 403 comprises a transmitter/receiver operable to communicate wirelessly with external devices such as an analysis server, personal computer, mobile telephone, or blood glucose monitor. Accordingly, once a complete set of tests have been completed, the CPU 605 can cause the display 409 to prompt a user to indicate, via the input buttons 411 or 413, whether the data stored in the memory 607 should be transmitted to an external device via the transmitter/receiver. Preferably, the transmitter/receiver is operable to communicate wirelessly with external devices, although it will be appreciated that other suitable forms of communicating data with external devices may be used such as wired connection via suitable connector such as USB. The correlation log can then be analysed by the external device such as a personal computer or an analysis server for review by a clinician.

The test protocol using the force probe is now described.

Figure 9:
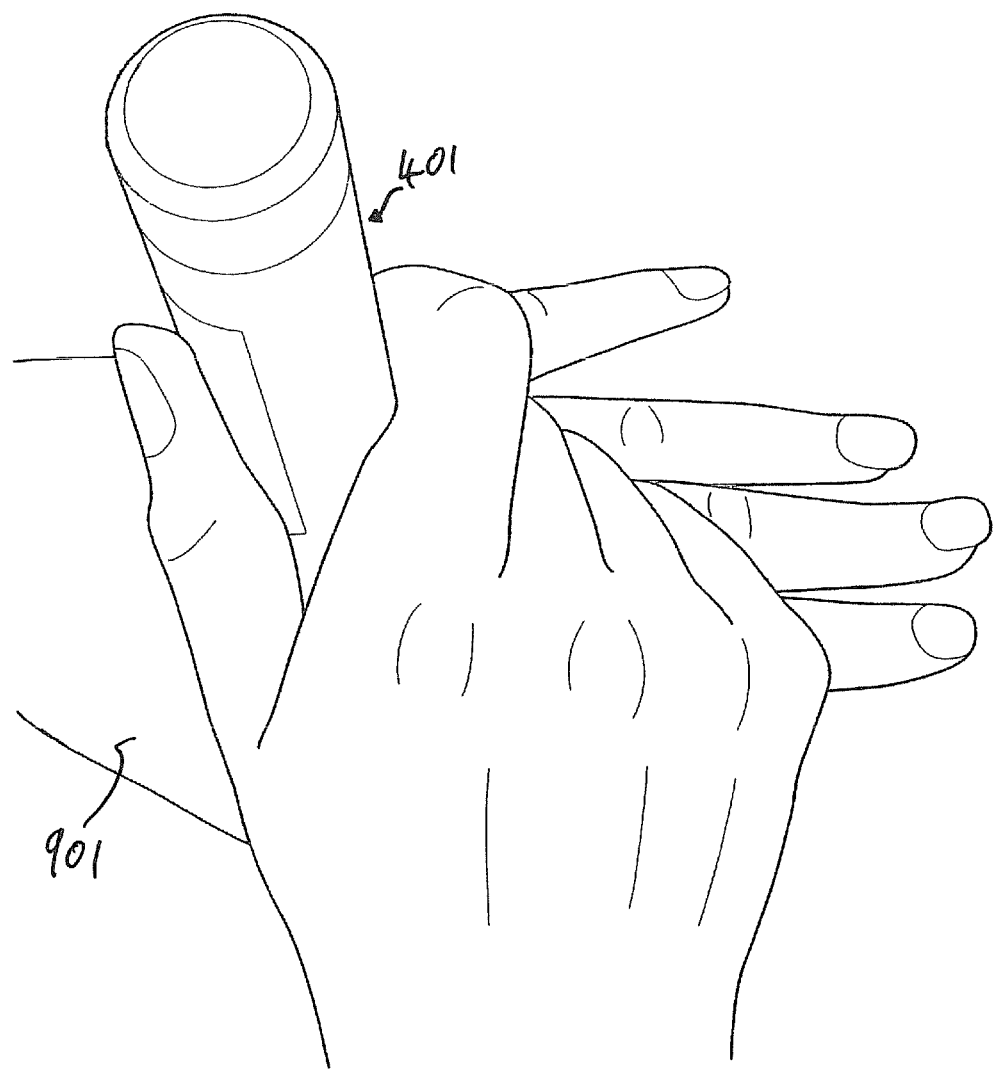
FIG. 9 shows the force transducer according to an embodiment of the invention being applied to the back of an operator's hand during initialisation of a test routine when a 10 g-force is applied.

FIG. 9 shows a schematic diagram showing a situation in which a testing procedure is carried out with the force transducer 401 by performing the following steps:

1. A fresh tip is inserted into the probe of the force transducer 401 and the tip 517 of the probe 407 is applied to a dorsal surface of an operator's or clinician's hand 901 so as to demonstrate to the patient that the device is neither a needle nor a noxious stimulus.
2. While keeping the tip of the probe in contact with the back the operator's hand 901, the transducer is operated by the operator applying downward pressure at a rate of approximately 10 mm s$^{-1}$ until the LED 701 is illuminated green (passive mode). Alternatively, in the active mode, the operator applies the tip 517 of the probe 407 to back of their hand so as to displace the probe from the preload position. The force transducer then causes the actuator to cause the predetermined force to be applied to the operator's hand by exerting a force on the biasing element.
3. Once the achieved, the operator releases the pressure immediately.
4. In the passive mode, this process is repeated a further two times, once with the 'pressure' threshold level (i.e. green LED illumination) and once with the 'over-pressure' threshold (i.e. red LED illumination).
5. Once the force transducer has been demonstrated to the patient, the operator carries out the steps 2 and 3 above in respect of selected test areas for either the passive or active mode on, for example, the patient's hand, arm, or foot.

Figure 10A:
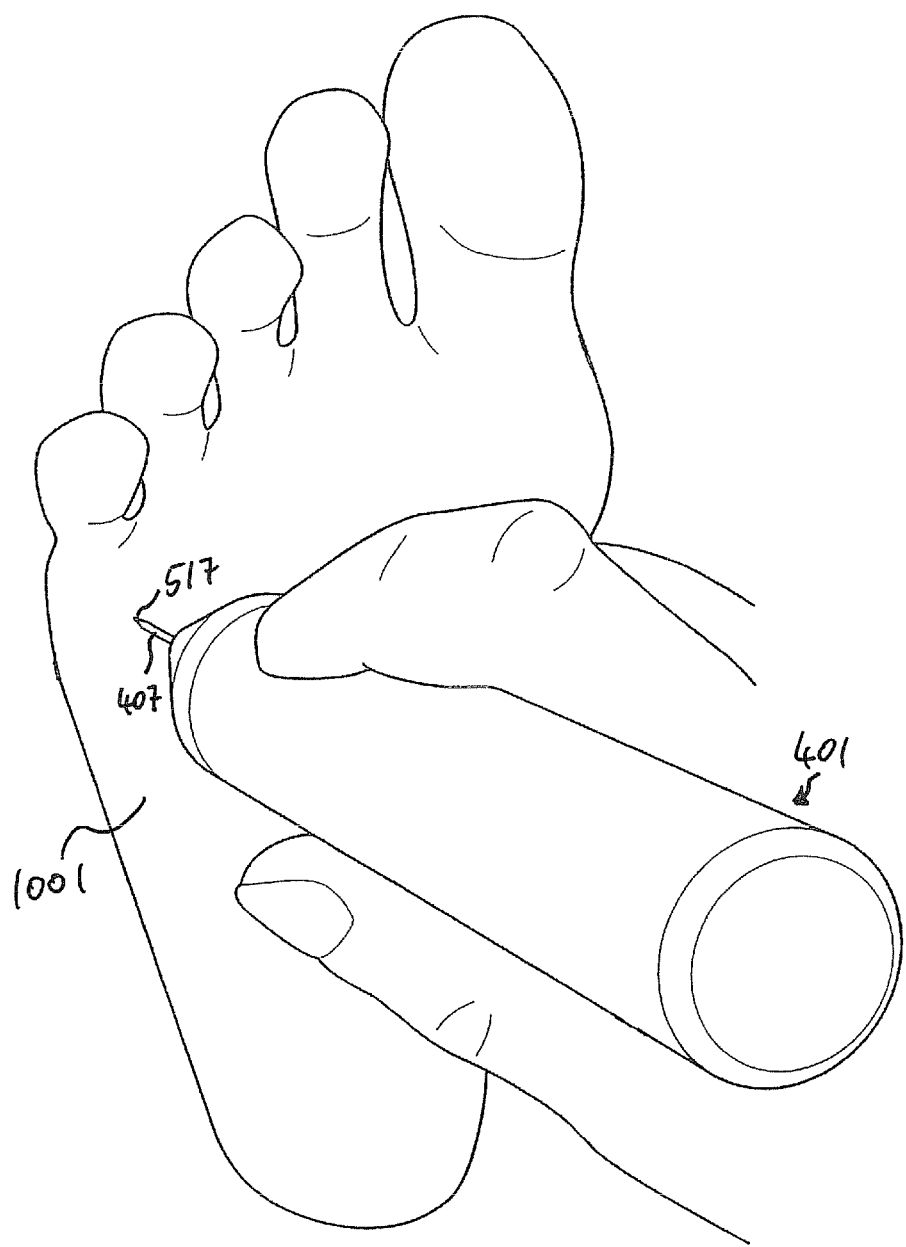
FIG. 10a shows the force transducer according to an embodiment of the invention being applied to the sole of a patient's foot during the test routine when a 10 g-force is applied.

FIG. 10A shows the tip 517 of the probe 407 of the force transducer 401 being placed onto a selected weight bearing site on the dorsal surface of the patient's foot 1001. The probe 407 is brought into contact with the weight bearing site, perpendicular to the plantar surface. In the passive mode, downward pressure is applied to the force transducer 401 as above, until the LED 701 is illuminated green. In the active mode, the downward pressure is applied to the force transducer 401 to displace the probe from the preload position. The force transducer then applies the predetermined force by exerting a force on the biasing element in dependence upon the force applied between the handle (housing) and the probe 407).

Figure 10B:
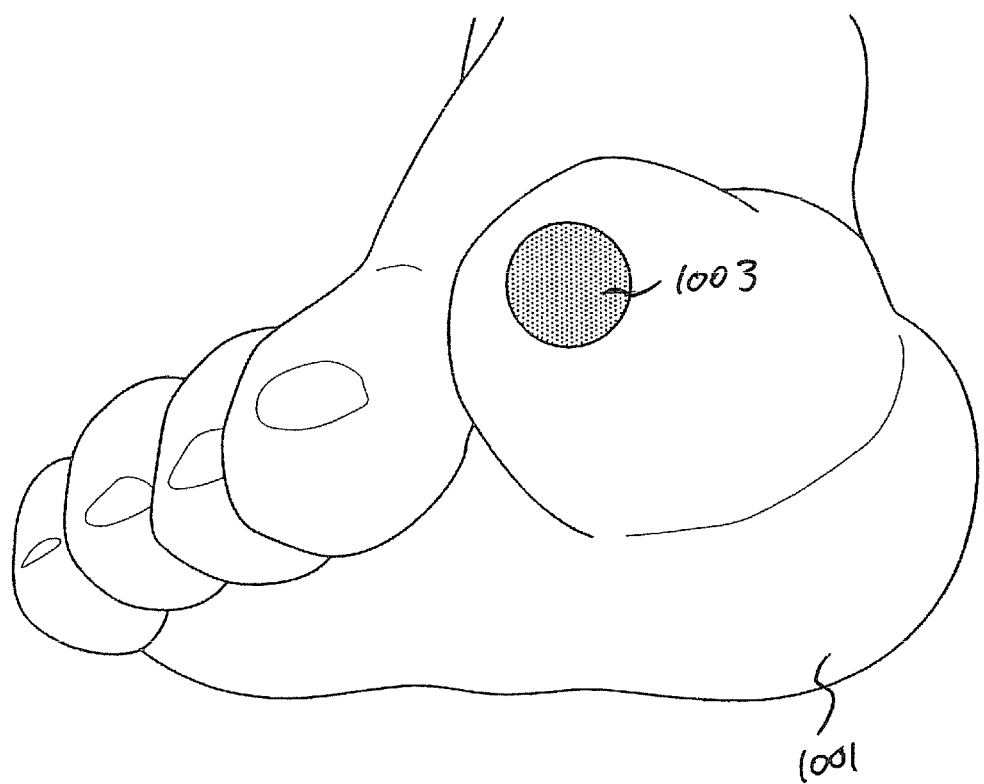
FIG. 10b shows the patient's foot from the front, illustrating key weight bearing sites at which the tip of the force transducer is applied to apply a 10 g-force load.
Figure 10C:
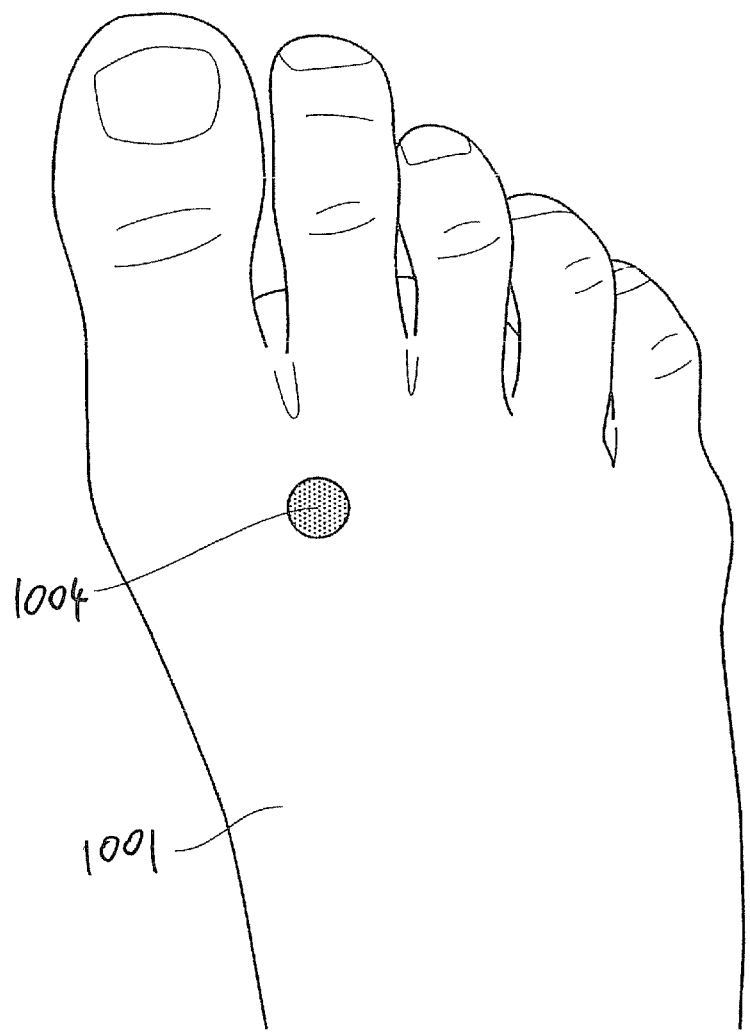
FIG. 10c shows the patient's foot from the top, illustrating a site at which the tip of the force transducer is applied to apply a 10 g-force load.
Figure 10D:
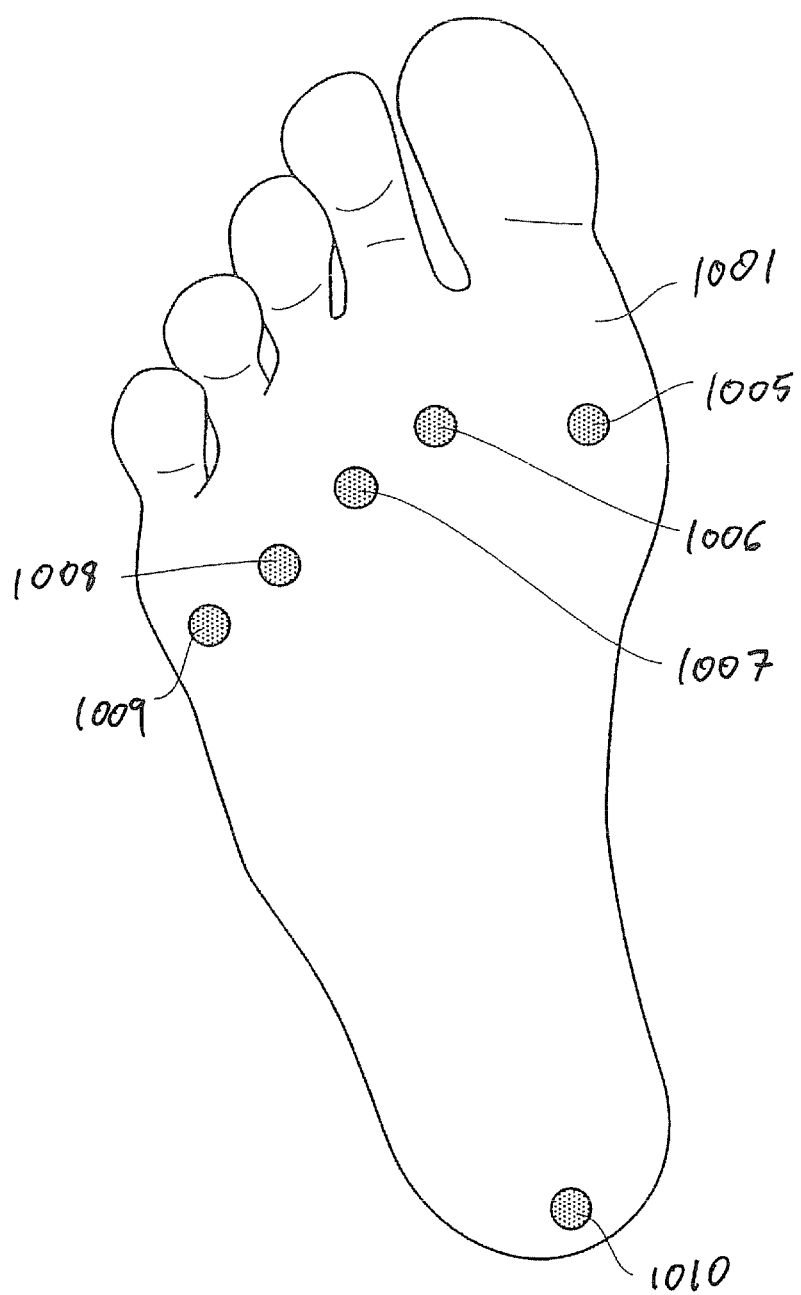
FIG. 10d shows the patient's foot from the bottom, illustrating the key weight bearing sites at which the tip of the force transducer is applied to apply a 10 g-force load.

FIGS. 10B, and 10D show examples of bony prominences (weight bearing sites) on the plantar surface of the foot where the force transducer 401 is typically applied in a random manner. FIG. 10C shows an additionally test area to which the force transducer may be applied.

FIG. 10B shows the apex of the hallux 1003 (tip of big toe).

FIG. 10C shows the dorsum of the foot 1004.

FIG. 10D shows the first metatarsophalangeal joint 1005, the second metatarsophalangeal joint 1006, the third metatarsophalangeal joint 1007, the fourth metatarsophalangeal joint 1008, the fifth metatarsophalangeal joint 1009 and the calcaneum 1010 (heel).

When the force transducer 401 is being used on a patient by an operator (clinician), the patient should be asked to close his/her eyes, so that the test is based on light touch response only and not unduly influenced by visual senses. The patient should typically be placed in a supine position, and should remove any shoes and hosiery, allowing a clinician ready access to the plantar surface of both feet.

When the force is applied to the plantar surface of the foot in a random manner to the weight bearing points (referred to as test areas or test sites), the patient is asked to say "yes", if any sensation is felt during the process. The clinician should not prompt the patient at any time, but should note any abnormal response. The patient's responses, both positive (i.e. "yes") and negative can be recorded on a data collection sheet.

Areas of callus are to be avoided during testing. If callus does exist at the test site, an alternative area located distally (towards the toes) from the original should be sought. Furthermore, areas of poor tissue vitality and/or open lesions are also to be avoided.

Once the test has been carried on a patient the used tip should be discarded in a suitable clinical waste dispenser.

Figure 11:
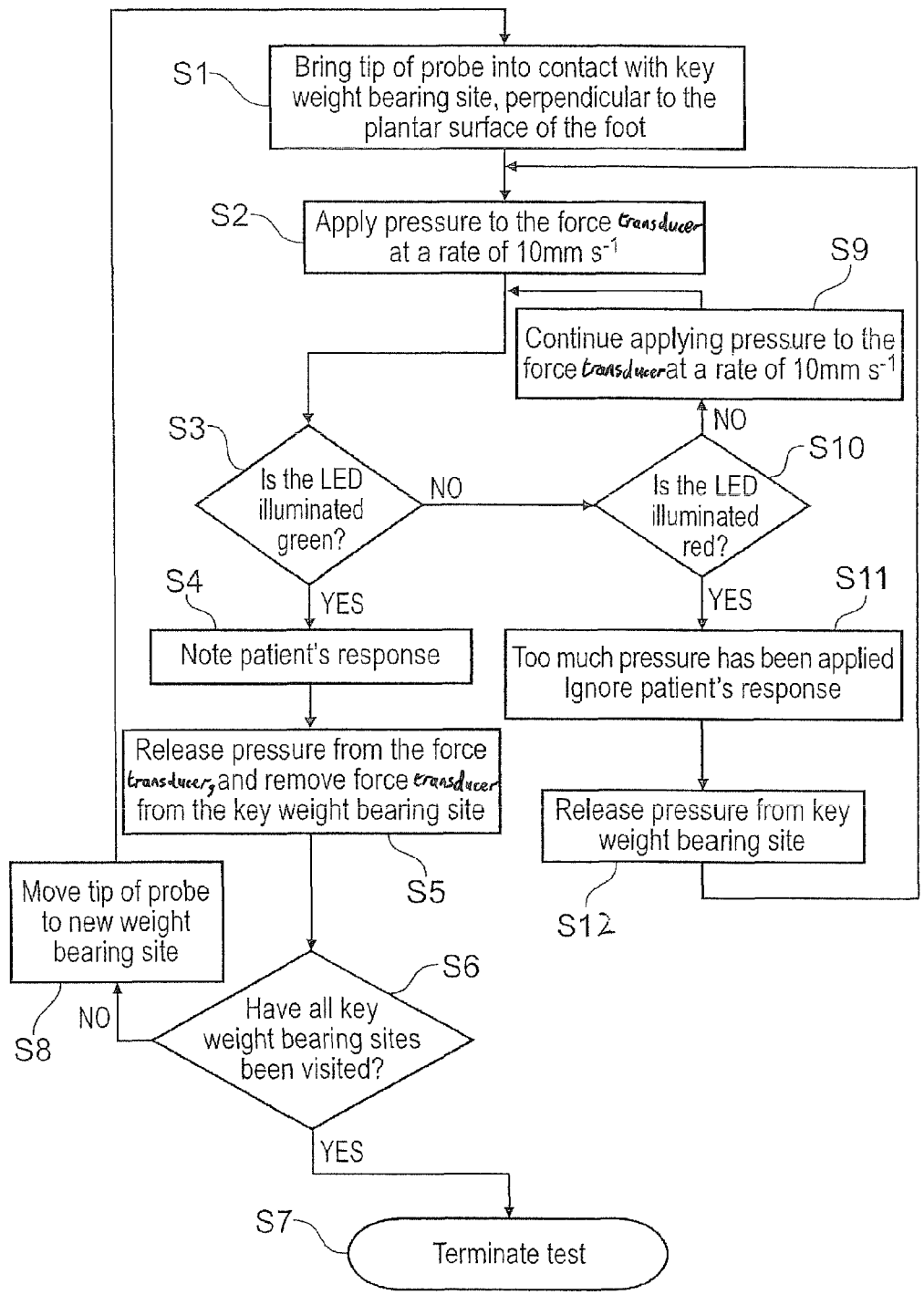
FIG. 11 shows a flow diagram for operating the force transducer during testing for the presence of diabetic peripheral neuropathy in patients.

FIG. 11 shows a flow diagram for operating the force transducer 401 in the passive mode.

In a Step S1, the tip 517 of the probe 407 is brought into contact with the plantar surface of the patient's foot at one of the selected weight bearing sites, as shown in FIGS. 10B to 10C. The probe 407 is brought into contact with the plantar surface of the foot perpendicular the plantar surface.

In a Step S2, the force transducer is moved towards the patient's foot by the operator (i.e. clinician) at a rate of approximately 10 mm s$^{-1}$, which is translated into a force being applied to the plantar surface of the foot. As the force is applied, the force loading on the weight bearing site is indicated by the force transducer 401 on the display 409.

In a Step S3, the illumination state of the visual indicator (i.e. the LED) is monitored to see it if is green. If the LED is not illuminated green, then the process flow jumps to a Step S10. If the LED is illuminate green, then the process flow jumps to a Step S4.

In a Step S4, the response to the applied load at the selected weight bearing site is noted. Both positive and negative responses are noted.

In a Step S5, the pressure is released from the force probe, thus removing the loading from the weight bearing site.

In a Step S6, if all of the selected weight bearing sites have been tested the process flow jumps to Step 8. If there are still weight bearing sites that are untested, the process flow jumps to a Step S1.

In a Step S7, all of the selected weight bearing sites are tested and the procedure is terminated. The force probe can then be switched to off. Once the test has been carried out on a patient the used tip should be discarded in a suitable clinical waste dispenser.

In a Step S8, the tip of the probe is moved to the location of a different, untested weight bearing site.

In a Step S9, the operator of the force transducer should continue to apply pressure to the force probe, because the pressure being applied is not enough to exert the pre-determined force load to the weight bearing site. This is known because the LED is not illuminated, therefore, the applied load must be less than the pre-determined 'pressure' load set within the force probe.

In the Step S10, the illumination state of the LED is monitored to see if it is red. If the LED is not illuminated red, then the process flow jumps to the Step S3, because the pressure being applied is not enough to exert the pre-determined force load to the weight bearing site. If the LED is illuminated red, then the operator is applying too much pressure, resulting in a load being applied to the weight bearing site which exceeds the pre-determined 'over-pressure' force load.

In a Step 11, the operator should not record the patient's response, because the load applied to the weight bearing site exceeds the predetermined 10 g-force (i.e. 98 mN) and therefore the response would be invalid for this particular test.

In a Step S12, the pressure on the force probe is released, such that it can be reapplied.

It will be appreciated that a similar test procedure as described above can also be used in a situation where the force transducer is operated in the active mode. In this case, the Steps S9 to S12 shown in FIG. 11 are not applicable. Additionally, the following steps are carried out in respect of the steps S2 and S3 described above.

The Step S2 is replaced with a step at which the probe is displaced from the preload position.

The Step S3 is replaced with a step in which the force transducer applies the predetermined force to the test area (key weight bearing site). Processing then proceeds to the step S4.

In some embodiments, at the Step S4 an entry into the correlation log can be generated as described above so as to provide an electronic record of the patient's responses.

Embodiments of the present invention in which a force transducer is used in a medical instrument for detecting an increased risk of diabetic neuropathic ulceration will now be described with reference to FIGS. 12 to 20.

Figure 12:
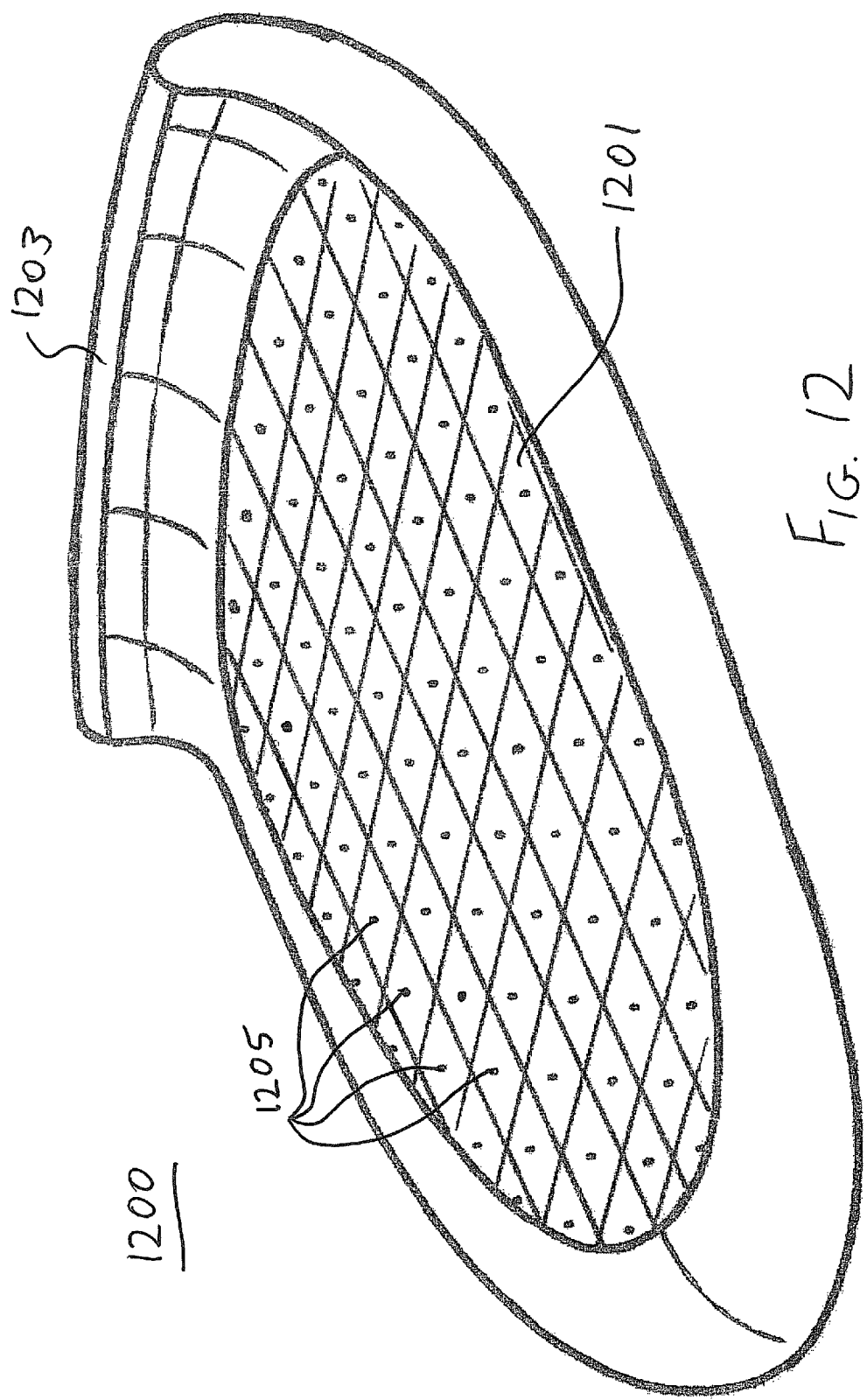
FIG. 12 shows a schematic perspective view of a floor mounted test device in accordance with an embodiment of the present invention.

FIG. 12 shows a perspective view of a medical instrument against which a body part of a patient may be placed so as to automatically apply a predetermined force to a plurality of test sites on, for example, a patient's foot. FIG. 12 shows a floor mounted test device 1200 (medical instrument) upon which a patient may place a selected body part, such as one or both feet, for testing for a degree of neuropathy. The floor mounted test device 1200 comprises a pressure sensing matrix 1201 upon which a patient may place the selected body part. In the following, the patient's foot will be used as an example of a suitable selected body part, although it will be appreciated that any suitable part of the patient's body could be tested. Additionally, the floor mounted test device 1200 comprises a toe end-stop 1203 against which a patient may place their toes. The toe end-stop 1203 comprises a vibrating element operable to vibrate at 128 Hz so as to cause vibrational stimuli to be applied to the patient's foot. This will be described in more detail below.

The pressure sensing matrix 1201 comprises a plurality of through holes, examples of which are labelled 1205 in FIG. 12, through which a probe of a force transducer may move so as to provide a stimulus to the underside of the patient's foot. Typically, the through-holes are arranged in a regular array although it will be appreciated that any other suitable arrangement could be used.

Figure 13:
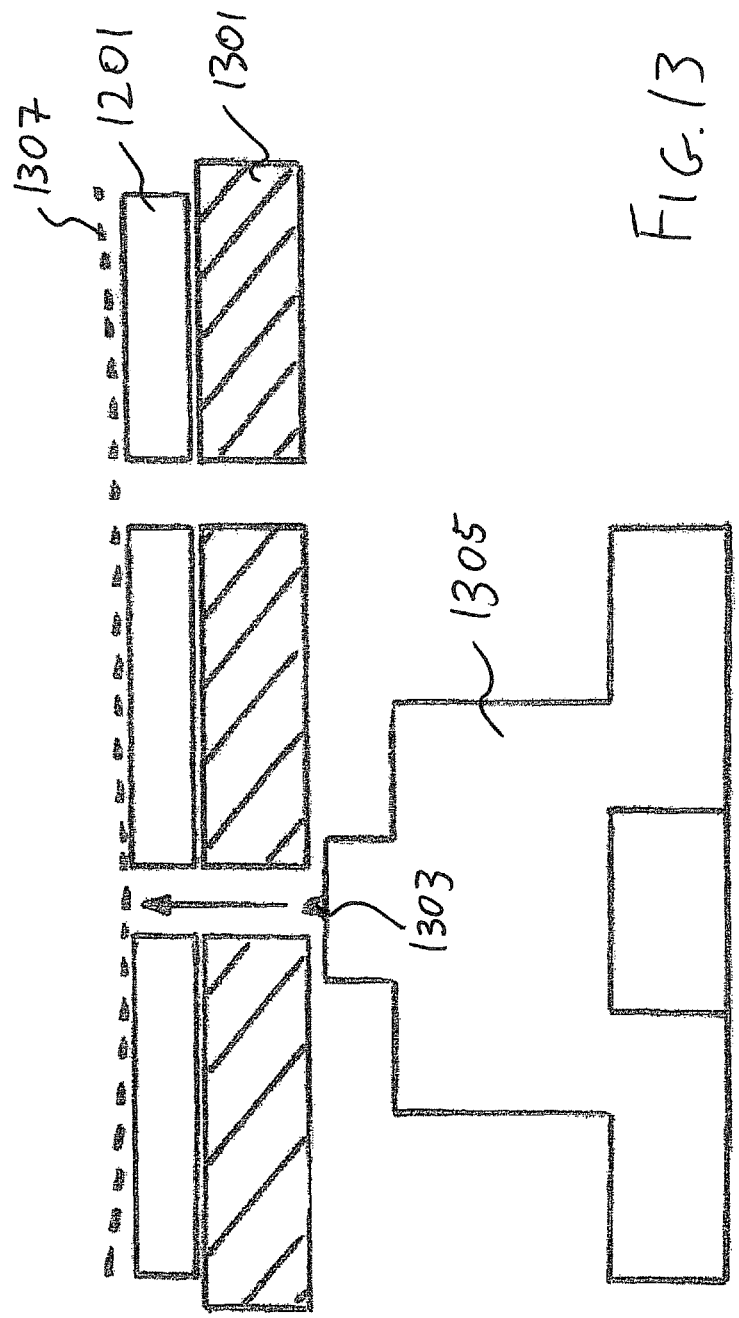
FIG. 13 is a cross-sectional view of the medical instrument of FIG. 12 showing an arrangement of a force transducer with respect to a surface of the test device in accordance with an embodiment of the present invention.

FIG. 13 shows a cross-sectional view of the floor mounted test device 1200 shown in FIG. 12. In particular, FIG. 13 shows the pressure sensing matrix 1201 in physical contact with a main body casing 1301 of the floor mounted test device 1200. The main body casing 1301 is mounted on a chassis which provides structural support and integrity of the floor mounted test device 1200. Preferably, the chassis is constructed from magnesium alloy or aircraft aluminium so as to provide a high strength for the device. The main body casing 1301 is typically made from Bayblend T85 (polycarbonate/ABS) with an outer coating of softlack paint. However, it will be appreciated that other suitable materials may be used for the chassis and the main body casing 1301.

As shown in FIG. 13, the through holes in the pressure sensing matrix are aligned with through holes in the main body casing 1301 so that a probe 1303 of a force transducer 1305 can apply a stimulus to a plantar surface of a patient's foot (indicated by the dashed line 1307). A position of the force transducer 1305 with respect to the through holes may be controlled and manipulated by a translation stage mounted on the chassis.

Preferably, the pressure sensing matrix 1201 comprises a piezo-electric sheet in the form of a plurality of piezo-electric transducers so as to allow a pressure map to be generated by the instrument as will be described in more detail below. However, the pressure sensing matrix could comprise any suitable pressure sensing devices.

Figure 14:
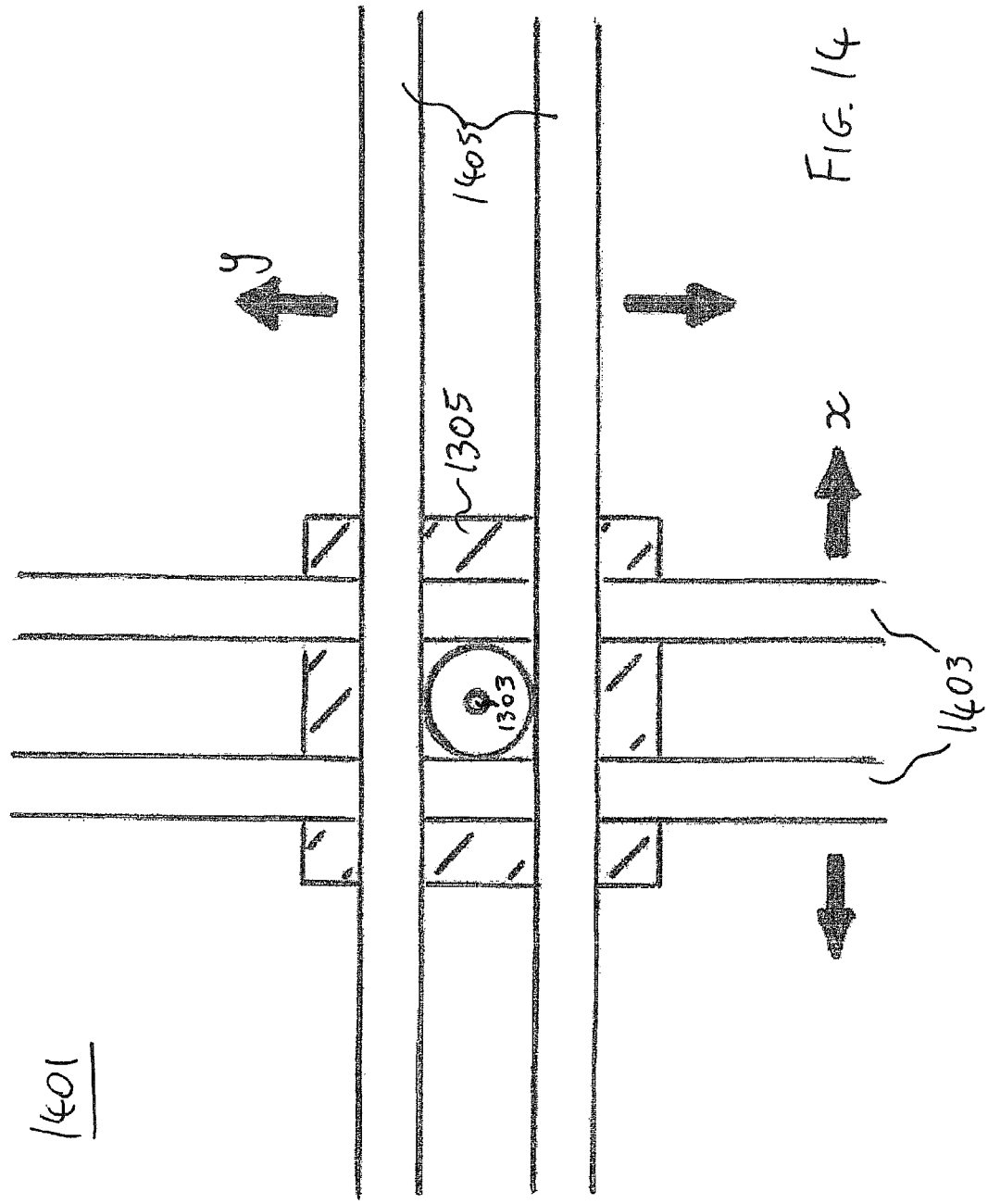
FIG. 14 is a plan view of a translation stage and a force transducer used in the test device of FIG. 12.

FIG. 14 shows a plan view of the force transducer 1305 mounted on a translation stage 1401. The translation stage 1401 comprises a pair of x-rails 1403 and pair of y-rails 1405. An upper region of the force transducer 1305 is captured between the x-rails 1403 and the y-rails 1405 of the translation stage 1401 so that motion in the x direction and/or y direction (as shown in FIG. 14) under the control of suitable motors (not shown) causes the force transducer 1305 to move accordingly. As mentioned above, the translation stage 1401 enables the force transducer to be moved to a position with respect to the through holes of the main body casing 1301 and the pressure sensing matrix 1201 so that the probe 1303 can provide a stimulus to the plantar surface of the patient's foot. The force transducer used in the floor mounted test device 1200 is substantially the same as that described with reference to FIG. 5 and is illustrated in cross-sectional view in FIG. 15.

Figure 15:
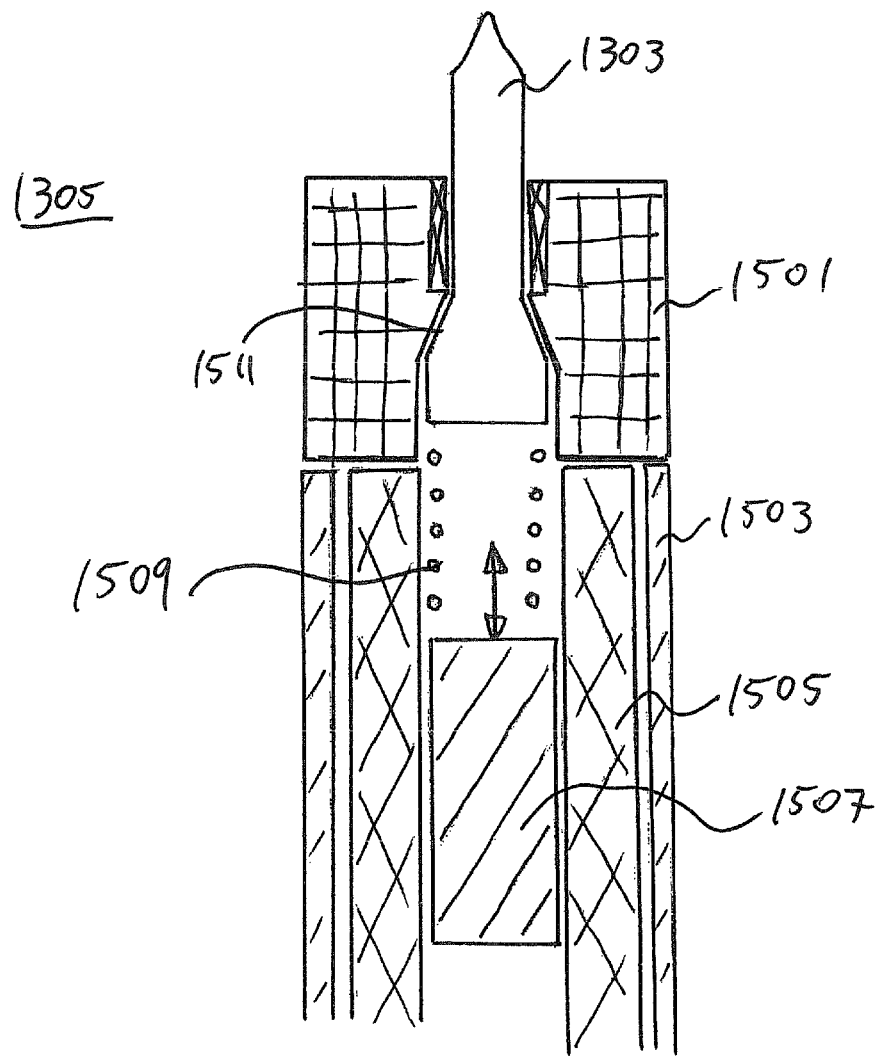
FIG. 15 is a schematic cross-sectional view of a force transducer in accordance with an embodiment of the present invention used in the test device of FIG. 12.

FIG. 15 is a schematic cross-sectional view of a force transducer used in the floor mounted test device 1200. In particular, the force transducer 1305 comprises the probe 1303, a nose 1501 having an aperture through which the probe 1303 may slide and move, and a housing 1503. The housing comprises an actuator and sensor module 1505 operable to drive an actuator piston axially within the housing with respect to the nose 1501. The actuator piston 1507 is in force transmitting communication with a compression spring 1509 which is in force transmitting with the probe 1303.

In embodiments of the present invention, the actuator piston 1507 comprises a sensor operable to detect a relative distance between the actuator piston 1507 and the probe 1303. The probe 1303 comprises a shoulder 1511 shaped so as to engage with a corresponding formation on the nose 1501. This prevents the probe 1303 from being pushed from the nose 1501 and the housing 1503 by the actuator piston 1507 as well as reducing the likelihood that a stick injury may occur to a patient.

In order to apply a predetermined force to the probe 1303 the actuator and sensor module 1505 is operable to control a position of the actuator piston 1507 within the housing 1503 with respect to the nose 1501 so as to control the relative distance between the actuator piston 1507 and the probe 1303 thus applying a known force to the probe 1303 as described above. The probe may be detachable or two-piece in a similar as that described for the force transducer 401 above so as to maintain hygiene.

In other words, the arrangement of FIG. 15 operates in a similar manner to the force transducer described with reference to FIGS. 4 to 11.

Circuitry used to control the floor mounted test device 1200 will now be described with reference to FIG. 16.

Figure 16:
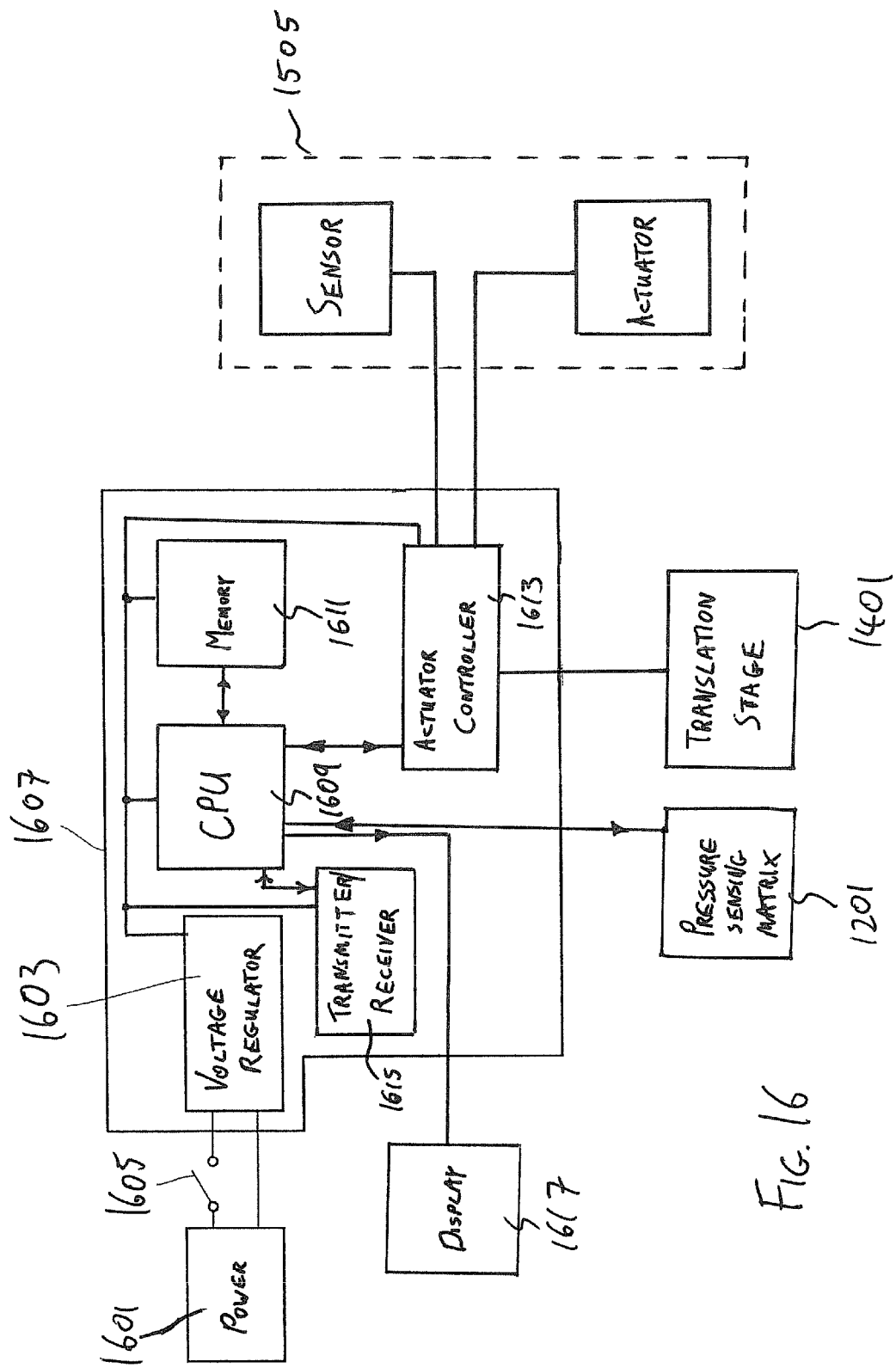
FIG. 16 is a schematic diagram of circuitry associated with the test device of FIG. 12 in accordance with an embodiment of the present invention.

FIG. 16 is a schematic diagram of functional units of the floor mounted test device 1200 illustrated in FIG. 12. In particular, FIG. 16 shows a power source 1601 which is electrically connected to a voltage regulator 1603 via a main power switch 1605. The voltage regulator 1603 is mounted on a printed circuit board 1607 which also comprises a central processing unit (CPU) 1609, a memory 1611, an actuator controller 1613, and a transmitter/receiver 1615. The voltage regulator 1603 provides power to the CPU 1609, the memory 1611, the actuator controller 1613, and the transmitter/receiver 1615. Additionally, the voltage regulator 1613 provides power to the actuator and sensor module 1505 as well as a display 1617 (not shown in FIG. 12). The CPU 1609 is operable to communicate and store data to the memory 1611 as well as sending control signals to the actuator controller 1613 for controlling the position of the actuator piston 1507 as well as a position of the force transducer 1305 with respect to the pressure sensing matrix through holes by sending appropriate commands to the translation stage 1401. The display 1617 may be used to display suitable user operation to the user. The CPU 1609 is also operable to control the vibrating element in the toe-end stop.

The transmitter/receiver 1615 is operable to communicate with external devices such as a personal computer or an analysis server. Preferably, the communication link is a wireless communication link, although it will be appreciated that any other suitable form of communication between the floor mounted test device 1200 and external devices may be used. In particular, the transmitter/receiver 1615 is operable to communicate with a user transponder which is illustrated in FIG. 17.

Figure 17:
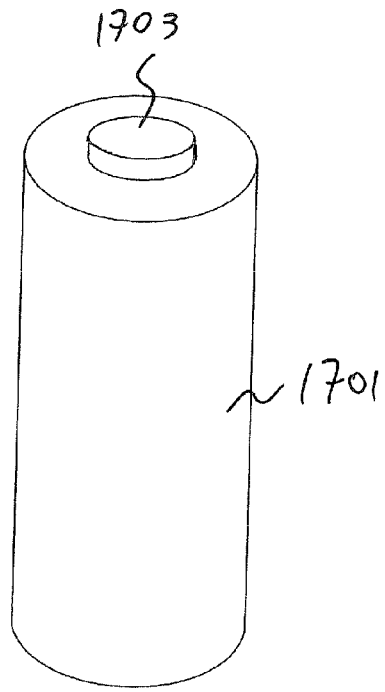
FIG. 17 shows a schematic view of a user transponder for communicating with the medical instrument of FIG. 12 in accordance with an embodiment of the present invention.

FIG. 17 shows a user transponder 1701 by which a user may communicate and indicate that they have felt a stimulus provided by the probe 1303. The transponder is operable to transmit a signal from the transponder 1701 to the transmitter/receiver 1615 which is indicative of a positive or negative response. It is to be understood that a positive response is taken to mean that a user has felt a stimulus or stimuli provided by the floor mounted test device 1200, and that a negative response is taken to mean they have not felt any stimulus or stimuli provided by the floor mounted test device 1200. To enable the user to communicate a positive response to the floor mounted test device 1200, the user transponder comprises a user input button 1703 which a user may activate in response to feeling a stimulus or stimuli from the floor mounted test device 1200. The user transponder 1701 accordingly transmits an appropriate signal from the user transponder 1701 to the transmitter/receiver 1615 via suitable communication links such as Bluetooth®, although other communication links could be used. A user interacting with the user transponder 1701 and the floor mounted test device 1200 is illustrated in FIG. 18.

Figure 18:
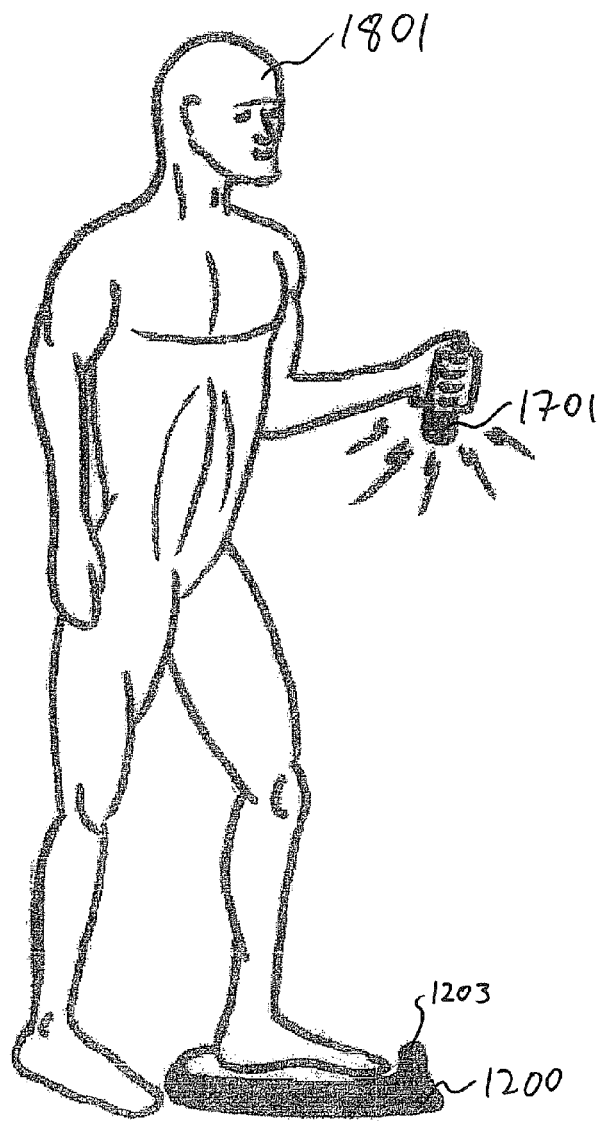
FIG. 18 shows a patient using the test device of FIG. 12 in conjunction with a user transponder in accordance with an embodiment of the present invention.

FIG. 18 shows a schematic view of a patient using the floor mounted test device 1200 in accordance with an embodiment of the present invention. In particular, FIG. 18 shows the user 1801 placing their foot on the floor mounted test device 1200 so that the big toe of their left foot is placed against the toe end-stop 1203 of the floor mounted test device 1200. When a user detects that a stimulus provided by the probe 1303 with the predetermined force, they may operate the user transponder 1701 so as to cause a positive response signal to be transmitted from the user transponder 1701 to the floor mounted test device 1200.

In an alternative embodiment, instead of through-holes, the floor mounted test device comprises a regular array of pins upon which the patient may position the body part to be tested. The translation stage can then cause the force transducer move to a location of a suitable test site or area and the CPU can cause the probe to be displaced towards the pins thus providing a predetermined force to a group of the pins and providing a stimulus to the patient.

A method of operation of the floor mounted test device 1200 will now be described with reference to FIG. 19.

Figure 19:
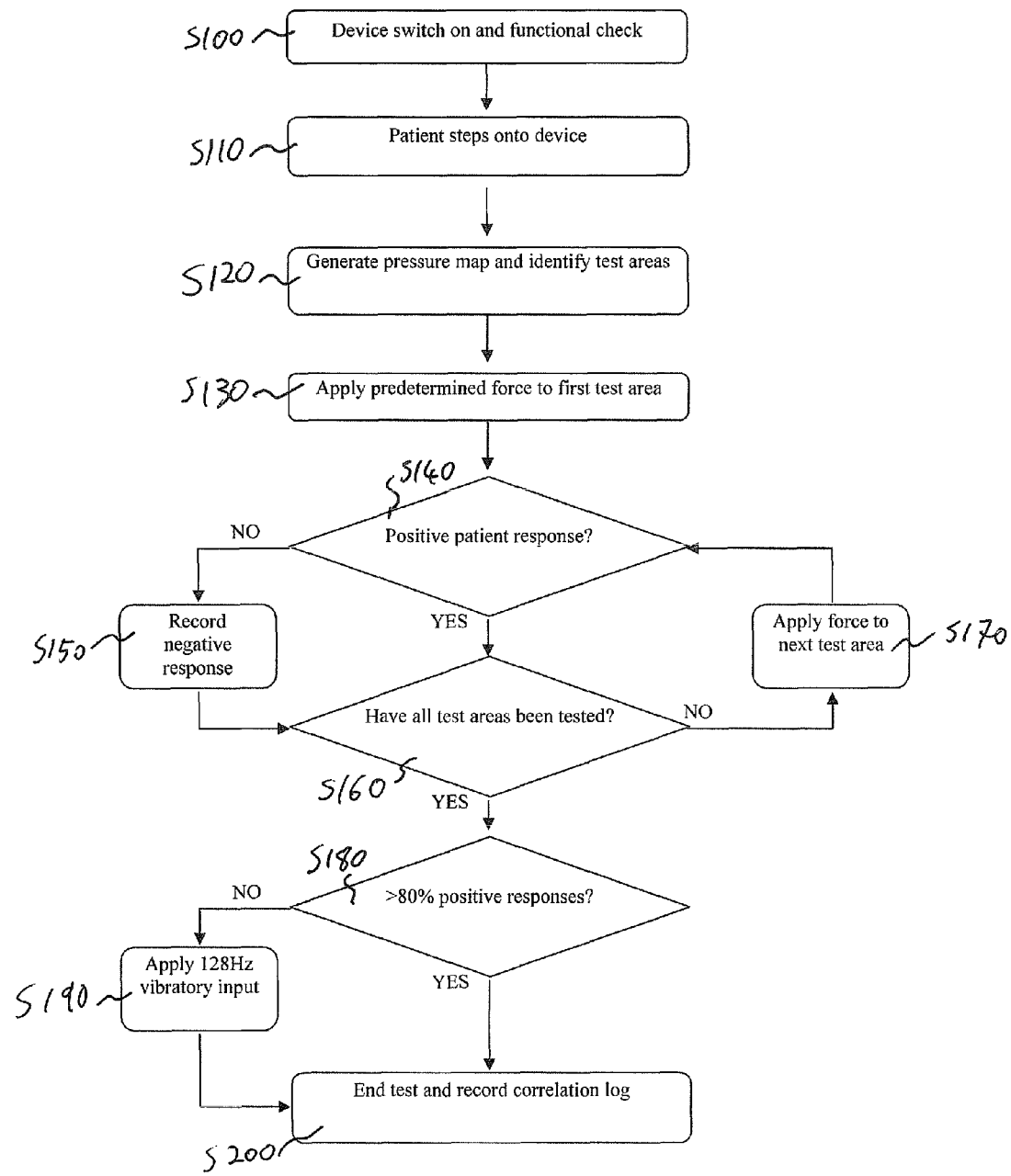
FIG. 19 shows a flow diagram of a method of operation of the test device shown in FIG. 12 in accordance with an embodiment of the present invention.

FIG. 19 shows a flow diagram of a method of operation of the floor mounted test device 1200 in accordance with an embodiment of the present invention.

At a step S100 a user may operate the master power switch 1605 so as to provide power to the floor mounted test device 1200. The CPU 1609 then causes a functional check to be carried out so as to ensure that all the components of the floor mounted test device 1200 are operating correctly. If the CPU 1609 detects that not all the components of the floor mounted test device 1200 are working correctly, then the CPU 1609 causes a suitable error message to be displayed on the display 1617 so as to inform the user of a fault. However, if the CPU 1609 determines that the components are working correctly, then processing proceeds to a step S110.

At the step S110, the patient (user) steps onto the pressure sensing matrix 1201 of the floor mounted test device 1200. Then at a step S120, the CPU 1609 is operable to detect regions of the pressure sensing matrix 1201 which are in physical contact with the plantar surface of the patient's foot, and to generate a pressure map indicative of pressure at regions of the pressure sensing matrix 1201 which are detected as being in physical contact with the plantar surface of the patient's foot.

The CPU 1609 is then operable to detect, by analysis of the pressure map, a location of suitable test areas with respect to the through holes of the pressure sensing matrix 1201 so as to generate a list of test areas to be tested. In embodiments of the present invention, this is done by carrying out an analysis of the pressure map to detect regions which have the highest pressure. However, it will be appreciated that other suitable methods for detecting a location of the body part with respect to the surface of the device could be used such as optical imaging. Additionally, the CPU 1609 is operable to detect any areas of the body part which are likely to correspond to compromised tissue (e.g. ulcerated regions) by analysis of the pressure map. Any regions of the pressure map which are detect as having a pressure less than a predetermined threshold are designated by the CPU 1609 as vulnerable areas and are excluded from list of test areas to be tested.

However, those regions which are detected as having highest pressure are designated suitable test areas and are included in the list of test areas. Typically, the test areas, correspond to those regions shown in FIG. 10D as these typically exert the highest pressure on the pressure sensing matrix. Alternatively, the pressure map may be analysed by the CPU 1609 using known pattern recognition techniques so as to detect suitable test areas (e.g. the test areas shown in, for example, FIGS. 8 and 10D).

Once the test areas have been identified, at a step S130 the CPU 1609 is operable to send control signals to the translation stage 1401 via the actuator controller 1613 so as to cause the force transducer 1305 to move to an appropriate through hole which corresponds to a first test area selected from the test areas identified at the step S120. The first area can be randomly selected by the CPU 1609 from the list of test areas, or it may be selected according to a predetermined protocol.

The CPU 1609 then causes the force transducer 1305 to apply a predetermined force to the probe 1303 by sending appropriate control signals to the actuator and sensor module 1505 via the actuator controller 1613. Once the CPU 1609 determines that the predetermined force has been applied to the probe 1303 then, at a step S140, the CPU 1609 is operable to detect whether there was a positive patient response independence upon a signal received from the user transponder 1701 via the transmitter/receiver 1615. If no signal is received from the user transponder 1701 within a predetermined time period, then at a step S150, the CPU 1609 generates a correlation log entry in the memory 1611 indicative that the first test area corresponds to a negative response. After processing at the step S150, processing passes to a step S160.

If, at the step S140, the signal from the user transponder 1701 indicates that there was a positive patient response to the stimulus provided by the predetermined force applied by the probe 1303, then the CPU 1609 generates an appropriate entry in a correlation log in the memory 1611 and processing passes to the step S160.

At the step S160, the CPU 1609 detects whether all test areas have been tested. If not all the test areas identified at the step S120 have been tested, then processing passes to a step S170.

At the step S170, the CPU 1609 controls the position of the force transducer 1305 by sending appropriate signals to the translation stage 1401 so as to move the force transducer 1305 to a through hole which corresponds to a next test area to be tested. Processing then passes back to the step S140 and a next corresponding entry in the correlation log is generated by the CPU 1609.

However, if at the step S160, all test areas have been tested, then, at a step S180, the CPU 1609 detects whether there are greater than a predetermined number of positive responses of the responses recorded at the steps S140 and the step S150. Typically, the CPU detects whether there are greater than a threshold number of positive responses recorded in the correlation log in the memory 1611. Typically, the threshold number is 80% of the number of test areas tested, although any other suitable threshold could be used. If there are fewer than 80% positive responses, then it is likely that the one or more test areas tested at the steps S170 and S130 correspond to regions of a patient's foot which are callused or lack sensation.

Therefore, at a step S190, the CPU 1609 is operable to control the vibrating element in the toe end-stop 1203 so as to apply a 128 Hz vibratory stimulus to the patient's big toe. However, it will be appreciated that any other suitable frequency may be used so as to provide stimuli to the patient's foot.

If, at the step S190, the patient detects stimuli provided by the toe end-stop 1203, then they may operate the user transponder 1701 to indicate they have felt the stimulus, thus causing the transponder to send a signal to the transmitter/receiver 1615 indicating that the patient has detected the stimulus provided by the floor mounted test device 1200.

Then, at a step S120, the CPU 1609 records this data in the correlation log in the memory 1611.

However, if at the step S180 the CPU 1609 detects there are more than 80% positive responses recorded in the correlation log stored in the memory 1611, processing proceeds to the step S200 and the correlation log is finalised and stored in the memory 1611.

In an embodiment, at the step S200, the CPU may cause the display 1617 to display an indication prompting the user to indicate whether they would like the correlation log to be transmitted to an external device such as a personal computer or analysis server. The user may then indicate their wishes using a suitable input device. The CPU 1609 then causes the data in the form of the correlation log stored in the memory 1611 to be transmitted to the external device via the transmitter/receiver 1615. This is illustrated with respect to FIG. 20.

Figure 20:
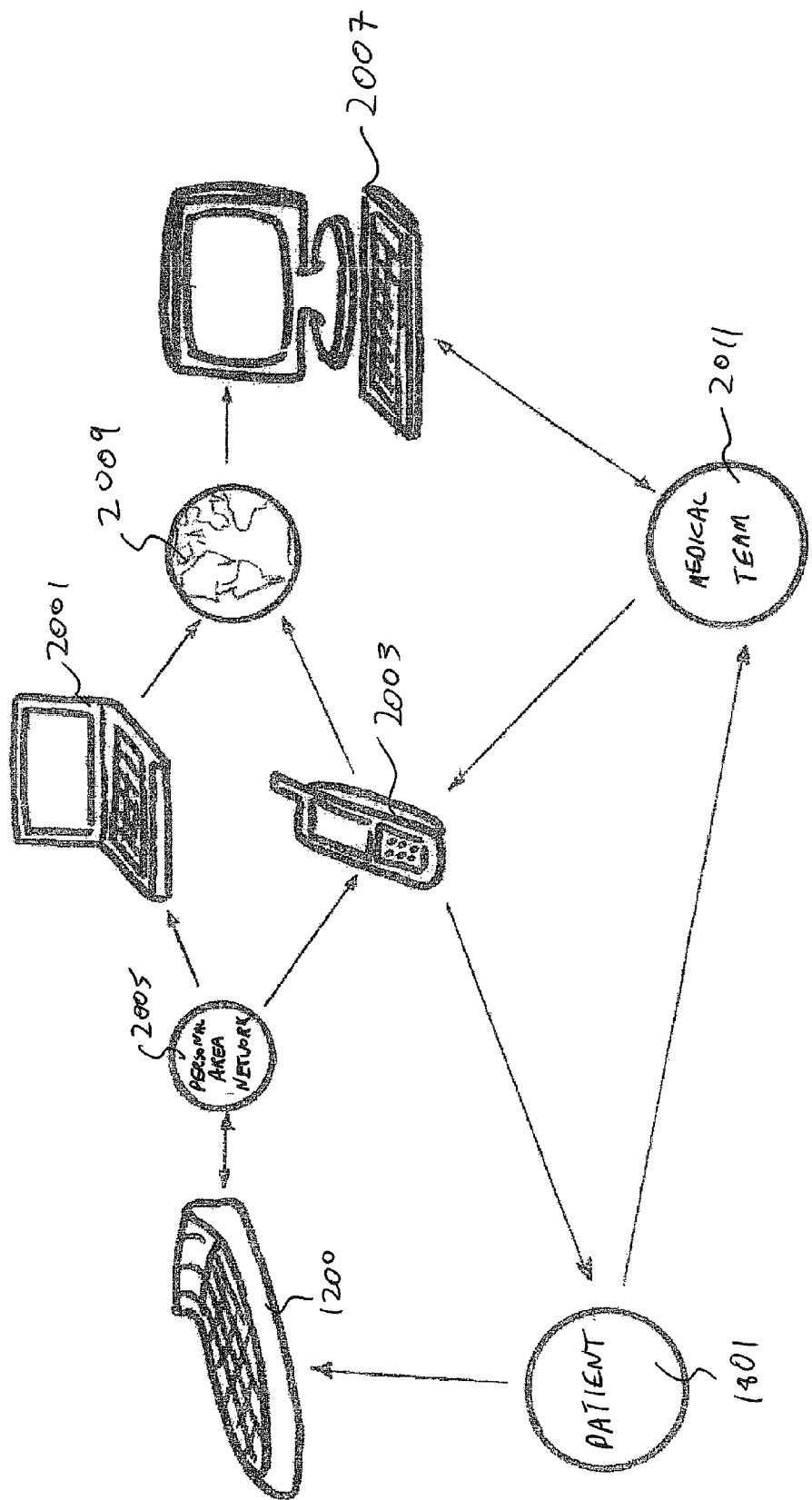
FIG. 20 shows a schematic diagram of the test device of FIG. 12 in communication with a plurality of other devices in accordance with an embodiment of the present invention.

FIG. 20 shows the floor mounted test device 1200 in communication with a personal computer or a mobile telephone device 2003 via a personal area network 2005. The personal computer 2001 may communicate with a mainframe or data analysis server 2007 via a network link such as the internet for analysis by a suitable medical team 2011. The medical team can then communicate with the patient 1801 via their telephone device 2003 independence upon the data received from the analysis server 2007. Accordingly, an increased risk of diabetic neuropathic ulceration can be diagnosed quickly and easily.

Additionally, the test device can communicate (synchronise) with a patient's blood-glucose monitor. The correlation log can then be compared by the monitor with historical blood chemistry. Furthermore, each time a patient takes a blood glucose reading, the synchronised floor mounted test device can prompt them to also test for any degree of neuropathy at predetermined periodic times. In embodiments, the monitor may analyse blood-glucose data to detect any abnormal readings that differ from an average reading. If there is greater than a threshold difference between the patient's current blood glucose level and the average blood glucose level for that patient (a glycaemic event), then the monitor can communicate with the test device so as to indicate to the patient that they should carry out a test for any degree of neuropathy and thus an increased risk of ulceration.

Furthermore, the test device can communicate any results of the neuropathy test to the patient's doctor or suitable clinical team thus enabling the patient to carry out home-monitoring of their degree of sensory neuropathy whilst still allowing them to communicate data to relevant health care professionals for monitoring. Additionally, it will be appreciated that the force transducer 401 could be used to communicate with external devices in a similar way as that described above for the test device 1200.

In the embodiments described above, the available projection of the probe from the nose is set to be less than the available stroke (travel) of the probe to mitigate and reduce any risk of stick injury occurring to a patient.

Additionally, in the embodiments described above, the predetermined force can be set by a user or be predetermined by the force transducer or the medical instrument to lie within a range of 5 g to 50 g (49 mN to 490 mN), although it will be appreciated that any or all of the above described embodiments could be used to apply any suitable force as appropriate, subject to the necessary modifications. It will be appreciated that, where a force is referred to in terms of grams (g), what is meant is the force which would be exerted if an object having that mass were allowed to accelerate freely under the force of gravity. In other words, F=ma (according to Newton's second law of motion), where m is the mass of the object, and a=9.8 ms$^{-2}$ so as to give the force in Newtons (N).

Furthermore, in the above described embodiments, the material of the nose of the force transducer is selected so as to provide a coefficient of friction which is substantially constant between the static regime and kinetic regime. Therefore, the predetermined force can typically be applied with a tolerance of ±5%.

Although illustrative embodiments of the invention have been described in detail herein with respect to the accompanying drawings, it is to be understood that the invention is not limited to those precise embodiments, and that various changes and modifications can be effected therein by one skilled in the art without departing from the scope and spirit of the invention as defined by the appended claims.

I claim:

1. A medical instrument comprising:
   a force transducer configured to apply a predetermined force, at a position selected from an array of predetermined possible positions within the medical instrument, as a stimulus to a test area of a body part of a patient;
   a processor configured to detect a location of said test area of said body part with respect to a current position of said force transducer and said array of predetermined possible positions;
   a translation element configured to move said force transducer to one or more positions in said array closest to said location of said test area detected by said detector; and
   a sample surface against which said body part of said patient may be placed, said sample surface comprising said array of predetermined possible positions;
   wherein said processor is configured to detect regions of said sample surface which correspond to a position of said body part with respect to said sample surface when said sample surface is in physical contact with said body part and to generate a pressure map indicative of pressure at those regions of said sample surface which are detected as being in physical contact with said body part, and wherein said processor is configured to detect said location of said test area on the basis of said pressure map.

2. An instrument according to claim 1, in which said processor is configured to detect said location of said test area with respect to said sample surface by detecting regions of pressure of said pressure map which have a pressure greater than a threshold pressure.

3. An instrument according to claim 2, in which said processor is configured to control said translation element so as to cause said force transducer to move to respective locations in said array of predetermined possible positions which substantially correspond to a plurality of respective test areas of said body part as determined by analysis of said pressure map.

4. An instrument according to claim 1, comprising a vibrating element for applying vibrations to said body part as a stimulus to said body part.

5. An instrument according to claim 1, comprising a receiver configured to receive, from a user input device associated with said patient, a signal indicating when said patient is aware of said stimulus provided by said instrument.

6. An instrument according to claim 5, comprising a user input device associated with said patient, said user input device being configured to transmit, to said receiver in response to input by said patient, said signal indicating when said patient is aware of stimuli provided by said instrument.

7. An instrument according to claim 5, in which said processor is configured to generate a correlation log indicating a correlation between reception of said signal and administration of said stimulus provided by said instrument.

8. An instrument according to claim 7, in which said processor is configured to generate said correlation log with respect to correlation between stimuli administered by said instrument at a plurality of test areas of said body part and said signals received from said user input device.

9. An instrument according to claim 7, comprising a memory configured to store said correlation log for analysis by a user.

10. An instrument according to claim 7, comprising a transmitter configured to transmit said correlation log to an analysis server for analysis.

11. An instrument according to claim 1, in which said body part of said patient is a foot of said patient, and said test area corresponds to a region on a plantar surface of said patient's foot.

12. A machine implemented method of detecting an increased risk of diabetic neuropathic ulceration using a force transducer operable to apply a predetermined force to a test area of a body part of a patient, said method comprising:
   providing a medical instrument as set forth in claim 1;
   detecting a location of said test area with respect to a position of said force transducer;
   moving said force transducer to said location of said test area;
   applying a predetermined force to said test area using said force transducer; and
   recording whether a response is received from said patient regarding touch sensation at said test area.

13. A method according to claim 12, comprising carrying out said method in respect of a plurality of selected test areas.

14. A method according to claim 12, in which said test area or selected test areas are on plantar surfaces of said patient's feet.

15. A method according to claim 12, in which said force transducer is configured to apply said predetermined force at a position selected from an array of predetermined possible positions and said force transducer is moved to one or more positions in said array closest to said detected location of said test area.

\* \* \* \* \*